(12) United States Patent
Ito et al.

(10) Patent No.: US 7,101,699 B2
(45) Date of Patent: Sep. 5, 2006

(54) SPHINGOLIPID CERAMIDE DEACYLASE GENE

(75) Inventors: Makoto Ito, Fukuoka (JP); Masako Furusato, Fukuoka (JP); Noriyuki Sueyoshi, Koga (JP)

(73) Assignee: Takara Bio Inc., Otsu (JP)

( * ) Notice: Subject to any disclaimer, the term of this patent is extended or adjusted under 35 U.S.C. 154(b) by 448 days.

(21) Appl. No.: 10/381,471

(22) PCT Filed: Sep. 26, 2001

(86) PCT No.: PCT/JP01/08344

§ 371 (c)(1),
(2), (4) Date: Apr. 29, 2003

(87) PCT Pub. No.: WO02/26963

PCT Pub. Date: Apr. 4, 2002

(65) Prior Publication Data

US 2004/0106183 A1     Jun. 3, 2004

(30) Foreign Application Priority Data

Sep. 26, 2000   (JP)   .............................. 2000-293181

(51) Int. Cl.
  *C12N 9/80*    (2006.01)
  *C12N 1/20*    (2006.01)
  *C12N 15/00*   (2006.01)
  *C07H 21/04*   (2006.01)

(52) U.S. Cl. ................ 435/228; 435/252.3; 435/320.1; 536/23.2

(58) Field of Classification Search ................ 435/228, 435/252.3, 320.1; 536/23.2
See application file for complete search history.

(56) References Cited

U.S. PATENT DOCUMENTS 6,428,999 B1    8/2002   Ito et al.

FOREIGN PATENT DOCUMENTS

| EP | 0 707 063 B1 | 4/1996 |
| EP | 0 940 409 A1 | 9/1999 |
| JP | 6-78782 A | 3/1994 |
| JP | 7-107988 A | 4/1995 |
| JP | 8-084587 A | 4/1996 |
| JP | 10-045792 A | 2/1998 |
| JP | 11-276177 A | 10/1999 |
| JP | 3035602 B2 | 2/2000 |
| WO | WO 98/03529 A1 | 1/1998 |

OTHER PUBLICATIONS

Ito, M., J. BIOL. CHEM., vol. 270, No. 41, pp. 24370-24374, (1995).
Abe, A., et al., J. BIOL. CHEM., vol. 271, No. 24, pp. 14383-14389, (1996).
Ito, M. et al.: J. Biol. Chem., Oct. 1995, vol. 270, No. 41, pp. 24370 to 24374.
Abe, A. et al.: J. Biol. Chem., Jun. 1996, vol. 271, No. 24, pp. 14383 to 14389.
Hirabayashi Y. et al.: J. Biol. Chem., 1998, vol. 103, No. 1, pp. 1-4.
Noriyuki Sueyoshi et al.; Journal of LIPID Research; vol. 38, No. 9, 1997, pp. 1923-1927.
Tetsuto Nakagawa et al.; Journal of Biochemistry, vol. 126, No. 3, Sep. 1999, pp. 604-611.
Makoto Ito et al.; Methods in Enzymology, vol. 311, pp. 297-303.
Makoto Ito et al.; Methods in Enzymology, vol. 311, pp. 682-689.
Masako Furusato et al.; Journal of Biological Chemistry, vol. 277, No. 19, May 10, 2002, pp. 17300-17307.
Ito, M. et al.: J. Biol. Chem., Oct. 1995, vol. 270, No. 41, pp. 24370 to 24374.
Abe, A. et al.: J. Biol. Chem., Jun. 1996, vol. 271, No. 24, pp. 14383 to 14389.
Hirabayashi Y. et al.: J. Biol. Chem., 1998, vol. 103, No. 1, pp. 1-4.

*Primary Examiner*—Tekchand Saidha
(74) *Attorney, Agent, or Firm*—Birch, Stewart, Kolasch & Birch, LLP

(57) ABSTRACT

A polypeptide possessing a sphingolipid ceramide deacylase activity; a nucleic acid encoding the polypeptide; a recombinant DNA comprising the nucleic acid; a carrier for introducing into a cell, carrying the nucleic acid or the recombinant DNA; a transformant harboring the nucleic acid or the recombinant DNA; an oligonucleotide probe or primer for the nucleic acid; a method for detecting the nucleic acid using the probe or the primer and a kit usable therefor; an antibody or a fragment thereof against the polypeptide; and a method for detecting the polypeptide using the antibody or a fragment thereof and a kit usable therefor. According to the present invention, there can be applied to engineering of sphingolipids, and to treatments for diseases such as diseases of nervous system (for instance, neurodegenerative diseases and the like), leukemia and wounds.

5 Claims, 1 Drawing Sheet

SPHINGOLIPID CERAMIDE DEACYLASE GENE

This application is the national phase under 35 U.S.C. § 371 of PCT International Application No. PCT/JP01/08344 which has an International filing date of Sep. 26, 2001, which designated the United States of America.

TECHNICAL FIELD

The present invention relates to a polypeptide possessing a sphingolipid ceramide deacylase activity and a nucleic acid encoding the polypeptide, and techniques using them. More specifically, the present invention relates to a polypeptide having an amino acid sequence of a sphingolipid ceramide deacylase, which is useful as a reagent for engineering of sphingolipids used for analyzing structures and functions of sphingolipids; a nucleic acid having a nucleotide sequence encoding the polypeptide; a method for producing a polypeptide having a sphingolipid ceramide deacylase activity by genetic engineering; a method for detecting the polypeptide and a kit therefor; and a method for detecting a gene encoding the polypeptide and a kit therefor.

BACKGROUND ART

In recent years, there have been remarked various physiological functions owned by sphingolipids as a constituent of the cell membrane lipids of eukaryotic organisms, as well as glycerolipids. Sphingolipid ceramide deacylase (SCDase), which acts on this sphingolipid to generate a fatty acid and a lysosphingolipid, is an enzyme that is not only useful in the elucidation of the physiological actions of sphingolipids but also very important in the field of engineering of sphingolipids such as preparation of derivatives of sphingolipids or labeling of sphingolipids.

Conventionally, an enzyme that acts on ceramide to hydrolyze the acid-amide bond between the sphingosine base and the fatty acid has been known as ceramidase (EC 3.5.1.23) [*Journal of Biological Chemistry*, 241, 3731–3737 (1966); *Biochemistry*, 8, 1692–1698. (1969); *Biochimica et Biophysica Acta*, 176, 339–347 (1969); *Science*, 178, 1100–1102 (1972)]. However, the enzyme is incapable of hydrolyzing the acid-amide bond between the sphingosine base and the fatty acid in the ceramide moiety of a sphingoglycolipid or sphingomyelin.

On the other hand, enzymes produced by microorganisms belonging to the genus *Nocardia*, the genus *Rhodococcus*, or the genus *Streptomyces* [*Journal of Biochemistry*, 103, 1–4 (1988); Japanese Patent Laid-Open No. Hei 6-78782; Japanese Patent Laid-Open No. Hei 7-107988] are capable of acting on a sphingoglycolipid to hydrolyze the acid-amide bond between the sphingosine base and the fatty acid, thereby generating a lysosphingoglycolipid and a fatty acid. However, all these enzymes have characteristics such that their substrate specificity is so narrow that they cannot act on all the sphingolipids.

In other words, enzymes produced by microorganisms belonging to the genus *Nocardia* act on what is so-called an "acidic glycolipid" such as GD1a, GM1, GM2 or GM3, but show little or no action on a neutral glycolipid. On the other hand, enzymes produced by microorganisms belonging to the genus *Rhodococcus* act on a neutral glycolipid but are incapable of acting on an acidic glycolipid. Enzymes produced by microorganisms belonging to the genus *Streptomyces* do not act on GM3 or a neutral glycolipid such as lactosylceramide or cerebroside. In addition, none of the enzymes described above act on sphingomyelin.

On the other hand, the SCDase derived from *Pseudomonas* sp. TK-4 strain [*Journal of Biological Chemistry*, 270, 24370–24374 (1995); Japanese Patent Laid-Open No. Hei 8-84587] has been known to have a broad spectrum of substrate specificity for a general sphingolipid including an acidic glycolipid, a neutral glycolipid, sphingomyelin and the like. In addition, this SCDase catalyzes not only a hydrolytic reaction of a sphingolipid to generate the corresponding lysosphingolipid and the corresponding fatty acid, but also a condensation reaction for synthesizing a sphingolipid from a lysosphingolipid and a fatty acid, and further catalyses a reaction for exchanging a fatty acid moiety of a sphingolipid with another fatty acid (WO 98/03529). Therefore, the SCDase serves as a very important tool in the field of engineering of sphingolipids, and is highly valued for its industrial applications. However, when the SCDase described above is industrially advantageously produced from a microorganism, it is necessary to add a ganglioside mixture to the culture medium during cultivation in order to induce the production of the enzyme existing in nature. For this reason, free fatty acids and lysosphingoglycolipids are produced in the culture medium, and enzymes other than the desired enzyme, such as sphingomyelinase, are concurrently produced, thereby making it difficult to perform the separation and purification of the desired SCDase from these lipids and co-existing enzymes.

In view of the above, in order to produce by genetic engineering the SCDase produced by *Pseudomonas* sp. TK-4, a gene for this SCDase has been cloned to prepare a transformant in which the gene is introduced (Japanese Patent Laid-Open No. Hei 11-276177). However, the activity of the SCDase produced in the transformant is low or at an undetectable level. Therefore, it has been difficult to produce SCDase by genetic engineering.

An object of the present invention is to provide a polypeptide possessing a sphingolipid ceramide deacylase activity, which is useful in the field of engineering of sphingolipids; a nucleic acid encoding the polypeptide; a production method capable of producing the polypeptide easily and in a large scale by genetic engineering; an oligonucleotide probe or primer, capable of specifically hybridizing to the nucleic acid; a method for detecting a sphingolipid ceramide deacylase gene using the oligonucleotide probe or primer; a kit usable therefor; an antibody or a fragment thereof, capable of specifically binding to the polypeptide of the present invention; a method for detecting a sphingolipid ceramide deacylase using the antibody or a fragment thereof; and a kit usable therefor.

DISCLOSURE OF INVENTION

Figure 1:
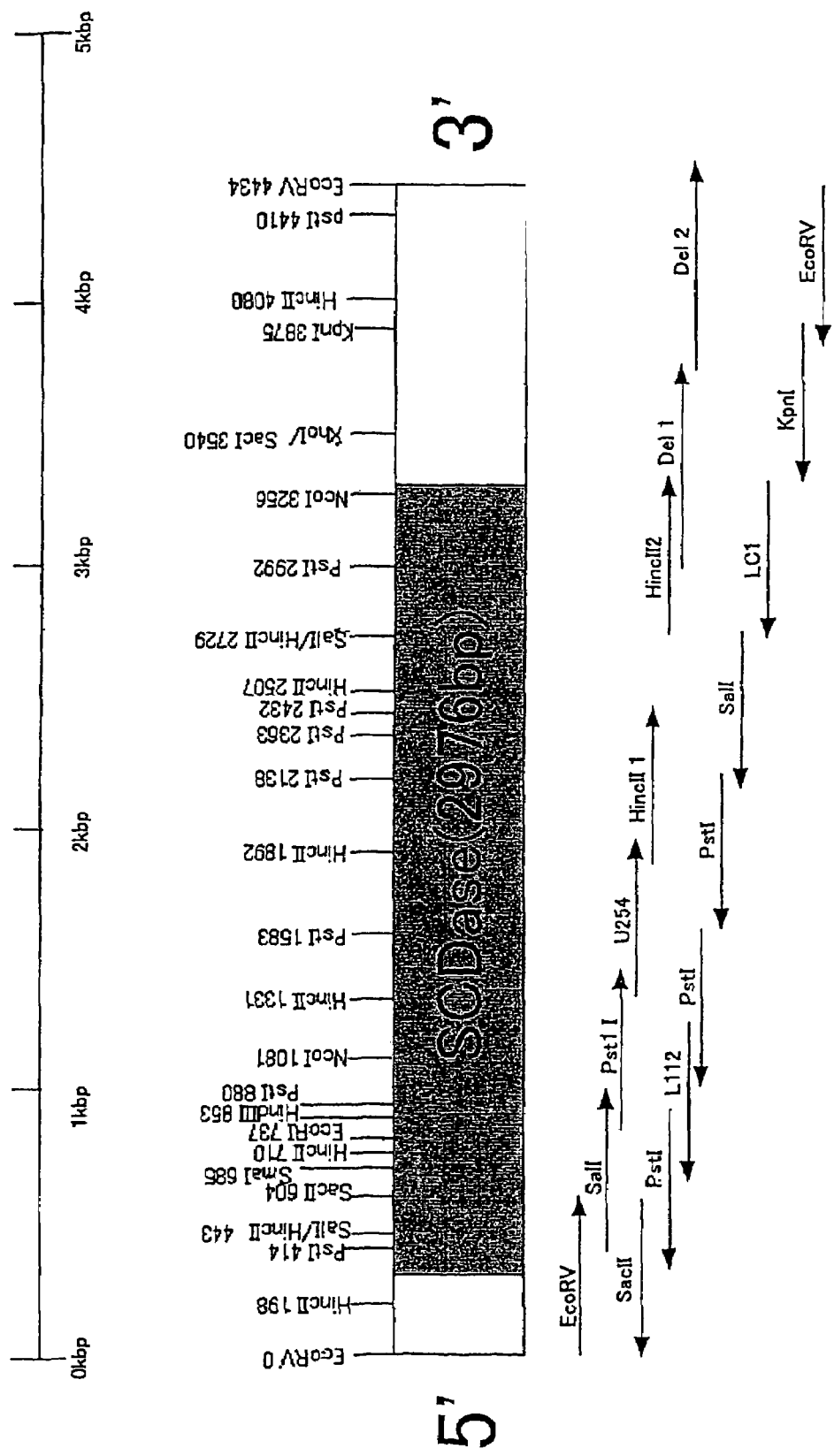
FIG. 1 is a restriction map of a DNA fragment insert in plasmid pSCD1.

As a result of intensive studies in order to isolate a gene encoding a polypeptide possessing a sphingolipid ceramide deacylase activity, the present inventors have succeeded in isolation of the gene encoding the polypeptide possessing a sphingolipid ceramide deacylase activity and elucidation of its nucleotide sequence. Further, the present inventors have established based on this finding a method capable of producing a sphingolipid ceramide deacylase activity having high purity easily and in a large scale; a method for detecting a polypeptide having a sphingolipid ceramide deacylase activity; and a method for detecting its genes. The present invention has been perfected thereby.

Concretely, the gist of the present invention relates to:

[1] a polypeptide selected from the group consisting of the following (a) to (c):
(a) a polypeptide having the amino acid sequence shown in SEQ ID NO: 20 or a part thereof;
(b) a polypeptide of which amino acid sequence has deletion, addition, insertion or substitution of at least one amino acid residue in the amino acid sequence shown in SEQ ID NO: 20; and
(c) an amino acid sequence having at least 25% sequence identity to the amino acid sequence shown in SEQ ID NO: 20, wherein the polypeptide possesses a sphingolipid ceramide deacylase activity;

[2] a nucleic acid selected from the group consisting of the following (A) to (H):
(A) a nucleic acid encoding a polypeptide having the amino acid sequence shown in SEQ ID NO: 20 or a part thereof;
(B) a nucleic acid encoding a polypeptide of which amino acid sequence has deletion, addition, insertion or substitution of at least one amino acid residue in the amino acid sequence shown in SEQ ID NO: 20;
(C) a nucleic acid encoding a polypeptide having at least 25% sequence identity to the amino acid sequence shown in SEQ ID NO: 20;
(D) a nucleic acid having the nucleotide sequence shown in SEQ ID NO: 19 or a part thereof;
(E) a nucleic acid having a nucleotide sequence having deletion, addition, insertion or substitution of at least one base in the nucleotide sequence shown in SEQ ID NO: 19;
(F) a nucleic acid capable of hybridizing under stringent conditions to the nucleic acid of any one of the above (A) to (E), or a complementary strand thereof;
(G) a nucleic acid having a nucleotide sequence different from the nucleic acid of any one of the above (A) to (F) via degeneracy; and
(H) a nucleic acid having a nucleotide sequence having at least 17% sequence identity to a nucleotide sequence of the nucleic acid of any one of the above (A) to (G), wherein the nucleic acid encodes a polypeptide possessing a sphingolipid ceramide deacylase activity;

[3] a recombinant DNA comprising the nucleic acid of the above item [2];

[4] a transformant harboring the nucleic acid of the above item [2] or the recombinant DNA of the above item [3];

[5] a method for producing a polypeptide possessing a sphingolipid ceramide deacylase activity, characterized by culturing the transformant of the above item [4] under conditions appropriate for expression of the sphingolipid ceramide deacylase, and collecting a polypeptide possessing a sphingolipid ceramide deacylase activity from the resulting culture;

[6] an oligonucleotide probe or primer, capable of hybridizing to the nucleic acid of the above item [2] under stringent conditions;

[7] the oligonucleotide probe or primer according to the above item [6], wherein the oligonucleotide probe or primer consists of at least 15 continuous nucleotides;

[8] a method for detecting a nucleic acid encoding a polypeptide possessing a sphingolipid ceramide deacylase activity, characterized by contacting a nucleic acid-containing sample to be tested with the oligonucleotide probe according to the above item [6] or [7], and thereafter detecting a hybrid of the nucleic acid with the oligonucleotide probe;

[9] a method for detecting a nucleic acid encoding a polypeptide possessing a sphingolipid ceramide deacylase activity, characterized by carrying out a nucleic acid amplification using the primer of the above item [6] or [7] with a nucleic acid-containing sample to be tested as a template sample;

[10] a kit usable for detection of a nucleic acid encoding a polypeptide possessing a sphingolipid ceramide deacylase activity, comprising the oligonucleotide probe and/or the primer according to the above item [6] or [7];

[11] an antibody or a fragment thereof, capable of specifically binding to the polypeptide of the above item [1];

[12] a method for detecting a polypeptide possessing a sphingolipid ceramide deacylase activity, characterized by contacting a polypeptide-containing sample to be tested with the antibody or a fragment thereof of the above item [11], and detecting a complex of the polypeptide with the antibody or a fragment thereof; and

[13] a kit usable for a detection of a polypeptide possessing a sphingolipid ceramide deacylase activity, comprising the antibody or a fragment thereof of the above item [11].

BEST MODE FOR CARRYING OUT THE INVENTION

As described above, the term "sphingolipid ceramide deacylase" as referred to herein is an enzyme that acts on a sphingolipid to hydrolyze into a sphingoid base and a fatty acid but shows little or no action on a ceramide.

In the present specification, the "polypeptide possessing a sphingolipid ceramide deacylase activity" may be referred to as "sphingolipid ceramide deacylase" in some cases.

Since the sphingolipid ceramide deacylase of the present invention has a broad spectrum of substrate specificity, the sphingolipid ceramide deacylase is useful in engineering of sphingolipids such as a method of analyzing physiological functions of glycolipids by cell engineering, a production of useful sphingolipids in a large scale, a conversion of functions of a sphingolipid, preparation of a sphingolipid probe, and creation of a novel sphingolipid. It is also useful in the applications to the treatment of diseases such as diseases of nervous system (e.g., neurodegenerative diseases etc.), leukemia, and wounds.

The sphingolipid ceramide deacylase activity can also, for instance, be determined according to the method described in *Journal of Biological Chemistry*, 270, 24370–24374 (1995). Concretely, for instance, 10 µl of an enzyme solution is added to 10 µl of a 50 mM acetate buffer (pH 6.0) containing 0.1% Triton X-100 and 10 nmol of GM1, and the reaction mixture obtained is incubated at 37° C. for a given time. Thereafter, the reaction mixture is boiled at 100° C. for 5 minutes to stop the reaction, and the reaction mixture is completely dried using a SPEEDVAC concentrator. Fifteen microliters of chloroform/methanol=2:1 (v/v) is added thereto, and the reaction product is dissolved by ultrasonic treatment. The dissolved product obtained is spotted onto a silica gel TLC plate (trade name: Silica Gel60 TLC plate, manufactured by Merck). After development with chloroform/methanol/0.2% $CaCl_2$ (5/4/1, v/v), orcinol-sulfuric acid is sprayed. After spraying, the TLC plate is heated on a 110° C. hot plate. Thereafter, the lyso-GM1 liberated and the unreacted GM1 are allowed to develop a color by the reaction.

The degradation ratio can be obtained by quantifying the spots corresponding to the liberated lyso-GM1 and the unreacted GM1 at a wavelength of 540 nm using a chromatoscanner [Shimadzu CS-9300, manufactured by Shimadzu Corporation], and calculating the degradation ratio by the equation:

"Degradation Ratio (%)=[Area of Liberated Lyso-GM1×100]/[Area of Liberated Lyso-GM1+Area of Unreacted GM1]"

on the bases of the obtained values.

One unit (U) of the sphingolipid ceramide deacylase activity is defined as the amount of enzyme that degrades 1 μmol of GM1 per one minute.

In the present invention, origins of the sphingolipid ceramide deacylase include, but are not particularly limited to, for instance, microorganisms such as bacteria, actynomecetes, yeasts, filamentous fungi, ascomycetes and basidiomycetes, or organisms such as plants, animals and insects. The sphingolipid ceramide deacylases derived from these origins are also encompassed in the scope of the present invention. Concretely, *Shewanella alga* G8 strain, a marine bacterium isolated from seawater, for instance, is suitable as a material for obtaining the sphingolipid ceramide deacylase of the present invention.

The above-mentioned *Shewanella alga* G8 can be obtained as described in the followings.

Samples collected from various places (seawater, river water, or body surfaces and gastrointestinal tracts of organisms living therein, and the like) are suspended in sterile physiological saline. Ten microliters of the suspension obtained is inoculated to 400 μl of a liquid medium containing 0.01% ceramide, 0.05% $NH_4Cl$, 0.05% $K_2HPO_4$, 0.1% yeast extract, 2.0% NaCl, and 0.01% TDC (sodium taurodeoxycholate), pH 7.0 in an Eppendorf tube and cultured with shaking at 25° C. for 4 days. Subsequently, the enzyme activity is determined by the method described above, and an active culture medium is selected. The selected culture medium is diluted with sterile physiological saline, and the dilution obtained is plated to a plate medium. After plating, the plate medium is cultured at 25° C. for 2 days to allow colonization. This operation is repeated until a single colony is obtained. Thus, *Shewanella alga* G8 capable of producing a sphingolipid ceramide deacylase can be isolated from the sample.

The above-mentioned *Shewanella alga* G8 is stocked at Ito's Laboratory, Department of Bioscience and Biotechnology, Kyushu University Graduate School of Bioresource and Bioenvironmental Sciences, and can be furnished upon request.

The sphingolipid ceramide deacylase of the present invention includes a polypeptide having the amino acid sequence shown in SEQ ID NO: 1 of Sequence Listing or a part thereof, and the like, preferably a polypeptide having an amino acid sequence having deletion of a C-terminal region in SEQ ID NO: 1 (amino acid numbers: 1 to 677) or a part thereof, and the like. Concretely, the sphingolipid ceramide deacylase includes a polypeptide having the amino acid sequence shown in SEQ ID NO: 20 or a part thereof. Here, the above-mentioned polypeptide having the amino acid sequence shown in SEQ ID NO: 20 is C-terminal deletion polypeptide of the above-mentioned polypeptide having the amino acid sequence shown in SEQ ID NO: 1, and exhibits a sphingolipid ceramide deacylase activity.

Accordingly, the sphingolipid ceramide deacylase of the present invention includes (a) a polypeptide having the amino acid sequence shown in SEQ ID NO: 1 or 20 (polypeptide having an amino acid sequence in which a C-terminal region in the naturally occurring sphingolipid ceramide deacylase is deleted) or a part thereof.

Here, the "polypeptide having a part of the amino acid sequence shown in SEQ ID NO: 1 or 20 (also referred to as a partial peptide)" may be a polypeptide found to have a sphingolipid ceramide deacylase activity similar to that of the polypeptide having the amino acid sequence shown in SEQ ID NO: 1 or 20, as determined by the above-mentioned method for determining the activity.

Concretely, the above-mentioned partial peptide can be obtained by expressing a polypeptide containing a given portion of the amino acid sequence shown in SEQ ID NO: 1 or 20 by a conventionally used gene engineering technique, subsequently determining the sphingolipid ceramide deacylase activity of the polypeptide by the above-mentioned method for determining the activity, thereby selecting a polypeptide exhibiting the activity. A method of expressing a partial peptide includes, for instance, a method comprising introducing a stop codon to a given position of a nucleic acid encoding the amino acid sequence shown in SEQ ID NO: 1 or 20 (for instance, SEQ ID NO: 2 or 19), and expressing the resultant; a method comprising cleaving a region corresponding to the desired partial peptide with restriction endonucleases or the like, and introducing the cleaved region into an appropriate expression vector, and expressing the resulting vector.

The present invention encompasses (b) a polypeptide of which amino acid sequence has deletion, addition, insertion or substitution of at least one amino acid residue in the amino acid sequence shown in SEQ ID NO: 1 or 20, as long as the polypeptide is found to have a sphingolipid ceramide deacylase activity similar to that of the polypeptide having the amino acid sequence shown in SEQ ID NO: 1 or 20, as determined by the above-mentioned method for determining the activity.

The above-mentioned "mutation" may be two or more mutations, as long as the mutation is a mutation such that the polypeptide obtained possesses a sphingolipid ceramide deacylase activity. Here, the "amino acid sequence having a mutation" is intended to include an amino acid sequence in which a naturally occurring mutation or an artificial mutation is introduced. The phrase "at least one" intended to include one or plural, or more.

The above-mentioned "mutation" can be generated by random mutagenesis method, site-directed mutagenesis method, and the like described below, using the nucleic acid of the present invention described below, concretely the nucleic acid encoding the amino acid sequence shown in SEQ ID NO: 1 or 20.

Furthermore, the present invention encompasses (c) a polypeptide having a sequence identity of at least 25%, preferably 30% or more, and more preferably 35% or more, to the amino acid sequence shown in SEQ ID NO: 20, as long as the polypeptide is found to have a sphingolipid ceramide deacylase activity similar to that of the polypeptide having the amino acid sequence shown in SEQ ID NO: 20, as determined by the above-mentioned method for determining the activity.

The above-mentioned polypeptide (c) has a sequence identity of at least 25%, preferably 30% or more, and more preferably 35% or more, as compared to the amino acid sequence shown in SEQ ID NO: 1.

The "sequence identity" as referred to herein is sequence similarity of residues between two polymeric molecules, concretely between two polynucleotides or two polypeptides. The above-mentioned "sequence identity" can be determined by comparing two amino acid sequences or nucleotide sequences aligned in the optimum state over the regions of the amino acid sequences to be compared or the nucleotide sequences to be compared. Here, the polynucleotides or polypeptides to be compared may have addition or deletion (for instance, gap, overhang, or the like), as compared to a reference sequence (for instance, consensus sequence or the like) for the optimum alignment of the two sequences.

The numerical value (percentage) of the sequence identity can be calculated by determining identical nucleic acid bases which are present in both of the sequences to determine the number of matched sites, thereafter dividing the above-mentioned number of the matched site by a total number of bases present within the region of the sequence to be compared, and multiplying the resulting numerical value by 100. An algorithm for obtaining optimal alignment and homology includes, for instance, local homology algorithm by Smith et al. [*Add. APL. Math.*, 2, p482 (1981)], homology alignment algorithm by Needleman et al. [*Journal of Molecular Biology*, 48, p443, (1970)], and homology search method by Pearson et al. [*Proceedings of the National Academy of Sciences of the USA*, 85, p2444 (1988)]. More concretely, there are included dynamic programming method, gap penalty method, Smith-Waterman algorithm, Good-Kanehisa algorithm, BLAST algorithm, FASTA algorithm, and the like.

The sequence identity between the polypeptides is determined, for instance, by using a sequence analysis software, concretely BLASTP, FASTA and the like. The sequence identity between the nucleic acids is determined, for instance, by using a sequence analysis software, concretely BLASTN, FASTA and the like. The above-mentioned BLASTP and BLASTN are generally accessible at homepage address: http://www.ncbi.nlm.nih.gov/BLAST/, and the above-mentioned FASTA is generally accessible at homepage address: http://www.ddbj.nig.ac.jp.

Also, the present invention encompasses a polypeptide having sequence homology of at least 25%, preferably 30% or more, and more preferably 35% or more to the amino acid sequence shown in SEQ ID NO: 20.

Furthermore, the present invention encompasses a polypeptide having a sequence homology of at least 25%, preferably 30% or more, and more preferably 35% or more to the amino acid sequence shown in SEQ ID NO: 1.

The above-mentioned polypeptide having sequence homology may be a polypeptide having a conservative substitution in the amino acid sequence of the sphingolipid ceramide deacylase. The above-mentioned "conservative substitution" encompasses a substitution with an amino acid having a similar characteristic (concretely, hydrophobicity, electric charge, pK, characteristics on steric structure); and a substitution with an amino acid that is only capable of altering the steric structure and folding structure of the polypeptide to an extent that the physiological activities inherently owned by the polypeptide are maintained. The conservative substitutions include, for instance, substitutions within the following groups: 1) glycine, alanine; 2) valine, isoleucine, leucine; 3) aspartic acid, glutamic acid, aspartic acid, glutamine; 4) serine, threonine; 5) lysine, arginine; 6) phenylalanine, tyrosine.

The above-mentioned "sequence homology" can be determined by sequence analyzing software programs such as BLAST [*Journal of Molecular Biology*, 215, 403–410 (1970)], and FASTA [*Proceedings of the National Academy of Sciences of the USA*, 85, 2444–2448 (1988)].

The nucleic acid of the present invention is a nucleic acid encoding the above-mentioned polypeptide possessing a sphingolipid ceramide deacylase activity, and having a nucleotide sequence encoding the amino acid sequence of the polypeptide possessing a sphingolipid ceramide deacylase activity. For instance, the nucleic acid includes a nucleic acid encoding a sphingolipid ceramide deacylase derived from *Shewanella alga* G8 strain. Concrete examples thereof include:

(A) a nucleic acid encoding a polypeptide having the amino acid sequence shown in SEQ ID NO: 1 or 20 or a part thereof;

(B) a nucleic acid encoding a polypeptide of which amino acid sequence has deletion, addition, insertion or substitution of at least one amino acid residue in the amino acid sequence shown in SEQ ID NO: 1 or 20;

(C) a nucleic acid encoding a polypeptide having at least 25% sequence identity to the amino acid sequence shown in SEQ ID NO: 1 or 20; and (D) a nucleic acid having the nucleotide sequence shown in SEQ ID NO: 2 or 19 or a part thereof.

The nucleic acid encoding the polypeptide having the amino acid sequence shown in SEQ ID NO: 20 and the nucleic acid having the nucleotide sequence shown in SEQ ID NO: 19 mentioned above each corresponds to, for instance, the nucleotide sequence of base numbers: 1 to 2031 in the nucleic acid having the nucleotide sequence shown in SEQ ID NO: 2.

The above-mentioned nucleic acid having the nucleotide sequence shown in SEQ ID NO: 2 can be obtained from *Escherichia coli* JM109 transformed with plasmid pSCD44 carrying the nucleic acids [*Escherichia coli* JM109/pSE5]. The "*Escherichia coli* JM109 transformed with plasmid pSCD44 carrying the nucleic acid having the nucleotide sequence shown in SEQ ID NO: 2" has been named and identified as *Escherichia coli* JM109/pSE5 and deposited under the Budapest Treaty with the accession number of FERM BP-7717 with the International Patent Organism Depositary, National Institute of Advanced Industrial Science and Technology, of which the address is AIST Tsukuba Central 6, 1-1, Higashi 1-chome, Tsukuba-shi, Ibaraki-ken 305-8566, Japan, since Aug. 24, 2001 (original date of deposit: Sep. 22, 2000).

In the present invention, the nucleic acid of the present invention encompasses (E) a nucleic acid having a nucleotide sequence having deletion, addition, insertion or substitution of at least one base in the nucleotide sequence shown in SEQ ID NO: 2 or 19, as long as the polypeptide is found to have a sphingolipid ceramide deacylase activity similar to that of the polypeptide having the amino acid sequence shown in SEQ ID NO: 1 or 20, as determined by the above-mentioned method for determining the activity. It is desired that the above-mentioned nucleic acid (E) is a nucleic acid having a nucleotide sequence having deletion, addition, insertion or substitution of at least one base in the nucleotide sequence shown in SEQ ID NO: 2 or 19 in a manner such that the nucleotide sequence is translated into an amino acid sequence.

Here, the "nucleotide sequence having substitution, deletion, addition or insertion" includes a nucleotide sequence in which naturally occurring mutation or an artificial mutation is introduced. The above-mentioned phrase "at least one" means to include one or plural, or more. The above-mentioned "mutation" can be generated according to random mutagenesis method, site-specific mutagenesis method, and the like described below.

The phrase "in a manner such that the nucleotide sequence is translated into an amino acid sequence" is intended to mean that the inherent open reading frame is not shifted by deletion, addition or insertion, or shifted only to an extent for maintaining the sphingolipid ceramide deacylase activity inherently owned.

Also, the nucleic acid of the present invention encompasses (F) a nucleic acid capable of hybridizing under stringent conditions to the nucleic acid of any one of the above-mentioned (A) to (E) or a complementary strand thereof, as long as the polypeptide is found to have a sphingolipid ceramide deacylase activity similar to that of the polypeptide having the amino acid sequence shown in SEQ ID NO: 1 or 20, as determined by the above-mentioned method for determining the activity.

In the above-mentioned hybridization, all or a part of the nucleic acid of any one of the above-mentioned (A) to (E) or a complementary strand thereof may be used as a probe. Here, "a part of the nucleic acid of any one of the above-mentioned (A) to (E) or a complementary strand thereof" may be those having a sequence specific to the nucleic acid of the present invention. Also, an oligonucleotide probe capable of specifically binding to the nucleic acid of any of the above-mentioned (A) to (E) may also be used as a probe.

Here, "hybridizing under stringent conditions" refers to those capable of hybridizing under the conditions described in *Molecular Cloning: A Laboratory Manual*, 2nd Ed., published by Cold Spring Harbor Laboratory in 1989, edited by T. Maniatis et al. Concretely, the conditions refer to those capable of hybridizing, for instance, under the following conditions. Concretely, a membrane immobilized with the nucleic acid is incubated together with the probe at 50° C. for 12 to 20 hours in 6×SSC (wherein 1×SSC is 0.15 M NaCl, 0.015 M sodium citrate, pH 7.0) containing 0.5% SDS, 0.1% bovine serum albumin (BSA), 0.1% polyvinyl pyrrolidone, 0.1% Ficol 400, and 0.01% salmon sperm DNA. After the termination of the incubation, the membrane is washed, starting at 37° C. in 2×SSC containing 0.5% SDS, and varying the SSC concentrations up to a range of 0.1-fold concentration and the temperature to a range of up to 50° C., until which the signal ascribed to the immobilized nucleic acid can be distinguished from the background, and thereafter the detection of the probe is carried out.

There can be confirmed that whether or not the nucleic acid newly obtained by the hybridization is the desired nucleic acid by examining the activity of the polypeptide encoded thereby by the above-mentioned method for determining the activity.

In addition, when the oligonucleotide probe is used, the above-mentioned "stringent conditions," but not particularly limited to, refer to conditions of carrying out incubation at a temperature of "Tm−25° C." for overnight in a solution containing 6×SSC, 0.5% SDS, 5× Denhardt's, and 0.01% salmon sperm DNA.

Tm of the oligonucleotide probe or primer is calculated, for instance, by the following equation (I):

$$Tm=81.5-16.6(\log_{10}[Na^+])+0.41(\% \ G+C)-(600/N) \quad (I)$$

wherein N is a strand length of the oligonucleotide probe or primer; and % G+C is a content of guanine and cytosine residues in the oligonucleotide probe or primer.

In addition, when the strand length of the oligonucleotide probe or primer is shorter than 18 nucleotides, Tm can be deduced from a sum of a product of the contents of A+T (adenine+thymine) residues multiplied by 2° C., and a product of the contents of G+C residues multiplied by 4° C., $[(A+T)\times 2+(G+C)\times 4]$.

The present invention encompasses (G) a nucleic acid having a nucleotide sequence different from the nucleic acid of any one of the above-mentioned (A) to (F) via degeneracy, as long as the polypeptide is found to have a sphingolipid ceramide deacylase activity similar to that of the polypeptide having the amino acid sequence shown in SEQ ID NO: 20, as determined by the above-mentioned method for determining the activity.

It has been known that there exist one to six kinds of codons (triplet base combinations) designating an amino acid on a gene for each kind of amino acids. Therefore, there can be a large number of nucleic acids each encoding a particular amino acid sequence, the number varying depending on the amino acid sequence. In nature, the nucleic acid does not exist in stable form, and it is not rare that a mutation of its nucleotide sequence takes place. The mutation on the nucleic acid may not alter the amino acid sequence encoded thereby (also referred to as silent mutation), in which case, it can be said that a different nucleic acid encoding the same amino acid sequence has been generated. Therefore, there cannot be denied the possibility that even when a nucleic acid encoding a particular amino acid sequence is isolated, a variety of nucleic acids encoding the same amino acid sequence are produced with generation passage of an organism containing the nucleic acid. Furthermore, it would not be difficult to artificially prepare a variety of nucleic acids each encoding the same amino acid sequence by means of various genetic engineering techniques.

Furthermore, the present invention encompasses (H) a nucleic acid having a nucleotide sequence having at least 17% sequence identity, preferably at least 20%, and more preferably at least 23% to a nucleotide sequence of the nucleic acid of any one of the above (A) to (G), as long as the polypeptide is found to have a sphingolipid ceramide deacylase activity similar to that of the polypeptide having the amino acid sequence shown in SEQ ID NO: 20, as determined by the above-mentioned method for determining the activity.

The sequence identity can be determined by the method described above.

The sphingolipid ceramide deacylase can be obtained in a large scale by the nucleic acid of the present invention. For instance, when a codon used on an inherent nucleic acid encoding the desired protein is low in usage in a host in the production of a protein by gene engineering, the expression level of the protein is sometimes low. In such a case, there have been tried to express the desired protein in a high level by artificially converting the codon into another one which is frequently used in the host without altering the amino acid sequence encoded (for example, Japanese Examined Patent Publication No. Hei 7-102146). It is as a matter of course possible to artificially produce a variety of kinds of nucleic acids each encoding a particular amino acid sequence and the nucleic acids can be also produced in nature.

Since the primary structure and the genetic structure of the sphingolipid ceramide deacylase have been elucidated according to the present invention, a gene encoding a polypeptide having at least one of deletion, addition, insertion or substitution in one or more amino acid residues in the amino acid sequence of the naturally occurring sphingolipid ceramide deacylase can be obtained by introducing a random mutation or a site-directed mutation into the gene of the present invention. Thus, there can be obtained a gene encoding a sphingolipid ceramide deacylase possessing a sphingolipid ceramide deacylase activity but with some differences in optimal temperature, stable temperature, optimal pH, stable pH, and other properties. Hence, these sphingolipid ceramide deacylases can be prepared by gene engineering.

As a method of introducing a random mutation, there can be employed, for instance, a method for generating a transition mutation in which cytosine base is substituted by uracil base with a chemical treatment using sodium hydrogen sulfite [*Proceedings of the National Academy of Sciences of the USA*, 79, 1408–1412 (1982)]; a method for lowering an accuracy of incorporation of nucleotide during DNA synthesis by carrying out PCR in a reaction mixture containing manganese [*Analytical Biochemistry*, 224, 347–353 (1995)]; and the like.

As a method for introducing site-directed mutation, there can be employed, for instance, a method utilizing amber mutation [gapped duplex method, *Nucleic Acids Research*, 12, 9441–9456 (1984)]; a method of utilizing a dut (dUTPase) gene and ung (uracil-DNA glycosilase) gene deficient host [Kunkel method, *Proceedings of the National Academy of Sciences of the USA*, 82, 488–492 (1985)]; a method by PCR utilizing amber mutation (WO 98/02535); and the like. Various kinds of kits for introducing site-directed mutation to a desired gene by these methods are commercially available, and a gene resulting from introduction of a desired mutation can be readily obtained by utilizing the kits.

The method for obtaining a sphingolipid ceramide deacylase gene derived from a microorganism using the hybridization method will be hereinafter described.

First, partial amino acid sequences of the sphingolipid ceramide deacylase are studied as the information for preparation of a probe for cloning the sphingolipid ceramide deacylase gene. The purified sphingolipid ceramide deacylase is directly subjected to amino acid sequencing by the Edman degradation method [*Journal of Biological Chemistry*, 256, 7990–7997 (1981)] according to a conventional method. Alternatively, a purified peptide fragment separated and purified from a peptide mixture obtained by limited hydrolysis by the action of a protease having high substrate specificity, such as lysylendopeptidase or N-tosyl-L-phenylalanyl chloromethyl ketone (TPCK)-trypsin, is subjected to amino acid sequencing.

An oligonucleotide to be used as a hybridization probe is designed and chemically synthesized on the basis of the information on the partial amino acid sequences thus elucidated.

Genomic DNA of a microorganism producing a sphingolipid ceramide deacylase is prepared and completely digested with an appropriate restriction endonuclease, and the resulting product is separated by agarose gel electrophoresis, and thereafter blotted onto a nylon membrane according to a conventional method. The hybridization of this DNA fragment on the nylon membrane and the above-mentioned synthetic oligonucleotide probe is carried out under ordinary conditions. For example, the nylon membrane is blocked in a pre-hybridization solution containing salmon sperm DNA, and thereafter incubated overnight together with a $^{32}$P-labeled synthetic oligonucleotide probe. After this nylon membrane is washed, an autoradiogram is prepared to detect a DNA fragment capable of hybridizing to the synthetic oligonucleotide probe.

The DNA fragment corresponding to the signal on the autoradiogram is extracted and purified from the agarose gel. The DNA fragment thus obtained is incorporated into a vector, for instance, a plasmid vector, by a commonly used method to give a recombinant DNA molecule. As the vector, various commercially available vectors can be used. Next, the recombinant DNA molecule is introduced into an appropriate host, for instance, *Escherichia coli*, to give a transformant. A method of transformation suitable for the vector used can be selected from the commonly used methods, for instance, a method described in *Molecular Cloning: A Laboratory Manual*, 2nd edition, and the like.

Next, a transformant having a fragment of the sphingolipid ceramide deacylase gene is selected. As the selection method, colony hybridization, plaque hybridization, and the like are used as appropriate depending on the kind of the vector. Also, there can be used PCR method in which the colony or plaque is directly used as a sample, or a method in which expression of the sphingolipid ceramide deacylase activity serves as an index.

A recombinant DNA molecule in which the fragment is incorporated is prepared from the transformant comprising a fragment of the sphingolipid ceramide deacylase gene, and the nucleotide sequence of the fragment is analyzed. The nucleotide sequence can be determined by an ordinary method, for instance, the dideoxy method. The determined nucleotide sequence is compared with the previously obtained partial amino acid sequences of the sphingolipid ceramide deacylase, the molecular weight of sphingolipid ceramide deacylase and the like, to determine whether or not the DNA fragment obtained is all or a part of the desired sphingolipid ceramide deacylase gene.

When the resulting DNA fragment does not contain a full-length of the sphingolipid ceramide deacylase gene, the desired full-length sphingolipid ceramide deacylase gene can be obtained by carrying out hybridization or the like after digesting genomic DNA with another restriction endonuclease in the same manner using a part of the fragment as a probe, to give a lacked partial sequence. The structure of the sphingolipid ceramide deacylase gene and the entire amino acid sequence of sphingolipid ceramide deacylase are determined from the thus-obtained DNA fragment comprising the sphingolipid ceramide deacylase gene.

In addition to the hybridization method described above, the sphingolipid ceramide deacylase gene of the present invention can also be obtained by a PCR method. For instance, the sphingolipid ceramide deacylase gene can be obtained by a PCR method using primers designed from an N-terminal amino acid sequence or internal partial amino acid sequence of the sphingolipid ceramide deacylase, or another PCR method using cassette DNA and cassette primers in addition to these primers.

Also, the nucleic acid having the nucleotide sequence shown in SEQ ID NO: 2 can be prepared by chemical synthesis on the basis of the same nucleotide sequence shown in SEQ ID NO: 2.

When a nucleic acid consisting of the nucleotide sequence shown in SEQ ID NO: 2 can be prepared by chemical synthesis, the above-mentioned nucleic acid can be synthesized by, for instance, enzymatically ligating oligonucleotides synthesized chemically by conventional phosphoramidite method or the like. Concretely, the DNA can be obtained by, for instance, the following steps:

(1) synthesizing each of several dozen kinds of oligonucleotides $A_n$ (wherein n is a positive integer) which can cover the nucleotide sequence shown in SEQ ID NO: 2, and complementary strand oligonucleotides $a_n$ (wherein n is a positive integer) having the same length as $A_n$, and consisting of a sequence complementary to a nucleotide sequence resulting from a shift with several bases at 3'-side or 5'-side on the $A_n$ sequence, wherein the complementary strand oligonucleotides $a_n$ are annealed with the oligonucleotides $A_n$, thereby generating double-stranded DNAs having 5'-cohesive end or 3'-cohesive end, by conventional chemical synthesis methods

[For instance, the above-mentioned $A_n$ are oligonucleotides each consisting of base nos: 1–20 ($A_1$), 21–40 ($A_2$), 41–60 ($A_3$), 61–80 (A4), 81–100 ($A_5$), 100–120 ($A_6$), 121–140 ($A_7$), 141–160 ($A_8$), . . . 2481–2862 ($A_{143}$) shown in SEQ ID NO: 2, and the above-mentioned $a_n$ are strands complementary to oligonucleotides each consisting of base nos: 1–23 ($a_1$), 24–43 ($a_2$), 44–63 ($a_3$), 64–83 ($a_4$), 84–103 ($A_5$) 104–123 ($a_6$), 124–143 ($a_7$), 144–163 ($a_8$), . . . 2844–2862 ($a_{143}$) shown in SEQ ID NO: 2.];

(2) phosphorylating each 5'-end of the oligonucleotides $A_n$ and each 5'-end of the corresponding complementary strand oligonucleotides $a_n$, obtained in the above step (1), by using ATP and conventional T4 polynucleotide kinase;

(3) annealing each of the oligonucleotides $A_n$ and each of the corresponding complementary strand oligonucleotides $a_n$, obtained in the above step (2), thereby giving several dozens of "double stranded DNA ($A_n a_n$) having 5'-cohesive end or 3'-cohesive end";

(4) dividing the double-stranded DNAs ($A_n a_n$) obtained in the above step (3) into several blocks corresponding to the nucleotide sequence shown in SEQ ID NO: 2 in an n-ascending order, and putting the double-stranded DNAs ($A_n a_n$) obtained in the above step (3) together in one tube corresponding to each block

[For instance, when the oligonucleotide consisting of the nucleotide sequence shown in SEQ ID NO: 2 can be prepared, there are set:

a tube for oligonucleotides $A_1$–$A_4$ and complementary strands $a_1$–$a_4$, a tube for oligonucleotides $A_5$–$A_8$ and complementary strands $a_5$–$a_8$, a tube for oligonucleotides $A_5$–$A_{11}$ and complementary strands $a_9$–$a_{11}$,

. . .
. . .
. . .

a tube for oligonucleotides $A_{140}$–$A_{143}$ and complementary strands $a_{140}$-$a_{143}$.];

(5) ligating the double-stranded DNAs for every tube in the above step (4) corresponding to each block, thereby giving double-stranded DNAs corresponding to each block;

(6) subjecting the double-stranded DNAs obtained in the above step (5) to gel electrophoresis, and extracting from a gel a band for the double-stranded DNA having the desired strand length corresponding to each block;

(7) putting together and ligating the double-stranded DNAs each having the desired strand length corresponding to each block obtained in the above step (6); and (8) examining the strand length on gel electrophoresis and/or performing nucleotide sequencing for the DNA obtained in the above step (7), thereby confirming that the resulting DNA is DNA consisting of the nucleotide sequence shown in SEQ ID NO: 2.

Next, the present invention will be concretely described taking as an example the case of a sphingolipid ceramide deacylase derived from *Shewanella alga* G8 strain.

First, the sphingolipid ceramide deacylase produced by *Shewanella alga* G8 strain is purified. *Shewanella alga* G8 strain is cultured at 25° C. in a commonly used liquid medium [PY medium (composition: 0.5% polypeptone, 0.1% yeast extract, 0.5% sodium chloride, pH 7.2)], the resulting culture supernatant is concentrated, and the concentrate is subjected to commonly used column chromatography, to purify a sphingolipid ceramide deacylase.

Next, partial amino acid sequences of the sphingolipid ceramide deacylase are studied. An N-terminal amino acid sequence of the above-mentioned sphingolipid ceramide deacylase has a variety of kinds of corresponding codons, so that the combinations of primer sequences would be enormous. Additionally, when PCR is carried out using the above-mentioned primers, a large number of nonspecific amplified products are generated. Therefore, it would be difficult to identify a product derived from the desired gene.

In order to obtain amino acid sequences having low degeneracy of the corresponding codons as the amino acid sequences for designing primers, the present inventors have carried out peptide mapping using reagents for limited proteolysis represented by protease or cyanogen bromide, and then tried to design primers. Hence, the present inventors have synthesized synthetic oligonucleotide primers on the basis of the amino acid sequences obtained, concretely each of oligonucleotide primer SS2a (SEQ ID NO: 9) designed from the N-terminal amino acid sequence C-603 (SEQ ID NO: 7) of the sphingolipid ceramide deacylase, and oligonucleotide primer SA3 (SEQ ID NO: 13) designed from the partial amino acid sequence C-606 (SEQ ID NO: 3). A specifically amplified DNA fragment can be obtained by carrying out PCR with the genomic DNA of *Shewanella alga* G8 strain as a template using the two kinds of primers described above. It is found that the fragment comprises a part of the gene encoding a sphingolipid ceramide deacylase by studying the nucleotide sequence of the fragment, and comparing the nucleotide sequence with partial amino acid sequences of the sphingolipid ceramide deacylase other than those described above, which have already been obtained.

By carrying out hybridization or the like using this amplified DNA fragment as a probe, the gene encoding a full-length of the sphingolipid ceramide deacylase can be cloned.

The entire nucleotide sequence of the thus-obtained gene encoding the sphingolipid ceramide deacylase derived from *Shewanella alga* G8 strain is shown in SEQ ID NO: 15. Also, the amino acid sequence of the sphingolipid ceramide deacylase deduced from this nucleotide sequence is shown in SEQ ID NO: 14. Further, from the comparison of this amino acid sequence with the N-terminal amino acid sequence of the sphingolipid ceramide deacylase derived from *Shewanella alga* G8 strain shown in SEQ ID NO: 7, it is found that the sphingolipid ceramide deacylase produced by the strain is converted, after translation, to a mature enzyme in which a N-terminal polypeptide consisting of 38 amino acids is removed. The amino acid sequence of this mature sphingolipid ceramide deacylase is shown in SEQ ID NO: 1, and the nucleotide sequence of the portion encoding the mature sphingolipid ceramide deacylase among the above-mentioned nucleotide sequences of the sphingolipid ceramide deacylase gene is shown in SEQ ID NO: 2, respectively. Since the above-mentioned amino acid sequence of the sphingolipid ceramide deacylase derived from *Shewanella alga* G8 strain and the nucleotide sequence encoding the amino acid sequence show no significant homology to commonly known amino acid sequences and nucleotide sequences of the sphingolipid ceramide deacylase, it is suggested that the enzyme derived from *Shewanella alga* G8 strain is a sphingolipid ceramide deacylase belonging to a new family.

Furthermore, a polypeptide in which 277 amino acids on a C-terminal side are deleted from the above-mentioned amino acid sequence shown in SEQ ID NO: 1 (C-terminal deletion polypeptide) also possesses a sphingolipid ceramide deacylase activity. The amino acid sequence of the above-mentioned C-terminal deletion polypeptide is shown in SEQ ID NO: 20, and its nucleotide sequence is shown in SEQ ID NO: 19.

As described above, in the present invention, since the entire nucleotide sequence of the nucleic acid encoding a sphingolipid ceramide deacylase has been elucidated, a DNA having high homology to the sphingolipid ceramide deacylase gene can be screened from a genomic DNA or cDNA library obtained from an organism other than *Shewanella alga* G8 strain by using all or a part of the sphingolipid ceramide deacylase gene as a hybridization probe. The hybridization can be carried out under commonly used conditions. For example, genes having various homologies can be obtained by carrying out hybridization under the stringent conditions described above by using a genomic DNA or cDNA library obtained from an organism other than *Shewanella alga* G8 strain.

On the other hand, the primer for PCR can be designed from the nucleotide sequence of the sphingolipid ceramide deacylase gene of the present invention. By carrying out PCR using this primer, a gene fragment having high homology to the gene of the present invention can be detected, or a whole gene can be obtained. Furthermore, an organism producing a sphingolipid ceramide deacylase can be detected.

In order to confirm whether or not the gene obtained by the above-mentioned hybridization or PCR is the gene encoding a polypeptide possessing a sphingolipid ceramide deacylase activity, the deduction can be made by comparing the nucleotide sequence of the gene obtained with the nucleotide sequence or amino acid sequence of the sphingolipid ceramide deacylase gene of the present invention. In addition, whether or not the gene obtained is the desired gene can be confirmed by producing a polypeptide encoded by the gene obtained using the method described below, and determining the sphingolipid ceramide deacylase activity.

A recombinant DNA can be prepared by ligating a nucleic acid encoding the polypeptide of the present invention, for instance, a nucleic acid having the nucleotide sequence shown in SEQ ID NO: 2 or SEQ ID NO: 19, with an appropriate vector. The recombinant DNA is also encompassed in the scope of the present invention.

The vector used in the preparation of the above-mentioned recombinant DNA includes plasmid vectors, phage vectors, viral vectors and the like. The above-mentioned vector can be appropriately selected depending upon the purpose of use of the recombinant DNA.

For instance, when the host is *Escherichia coli*, the vector includes plasmid vectors such as pUC118, pUC119, pBR322, pCR3 and pCMVSPORT; phage vectors such as λZAPII and λgt11. When the host is an yeast, the vector includes pYES2, pYEUra3 and the like. When the host is an insect, the vector includes pAcSGHisNT-A and the like. When the host is an animal, the vector includes pKCR, pEFBOS, cDM8, pCEV4 and the like. The vector may appropriately have elements such as an inducible promoter, a selectable marker gene or a terminator.

There may be used a vector capable of inducing and expressing a foreign gene; a vector capable of expressing as a fusion protein with a reporter gene product or the like, from the viewpoint of producing the polypeptide of the present invention easily and in a large scale.

The vector capable of expressing as a fusion protein includes glutathione S-transferase (GST) fusion protein vector carrying an appropriate promoter (lac promoter, tac promoter, trc promoter, trp promoter, CMV promoter, SV40 early promoter, or the like) which functions in a host cell (pGEX4T or the like); a vector carrying a tag (His tag, or the like) sequence, wherein the vector has the above-mentioned appropriate promoter or the like.

Furthermore, according to the nucleic acid of the present invention or the recombinant DNA of the present invention, there is provided a carrier for introducing into a cell, carrying the nucleic acid or the recombinant DNA. The carrier for introducing into a cell is also encompassed in the present invention. Concretely, the carrier for introducing into a cell according to the present invention is a carrier carrying the nucleic acid of the present invention or the recombinant DNA of the present invention. The above-mentioned carrier includes liposome, HVJ-liposome, dextran, calcium phosphate, gold particles and the like.

Also, a transformant can be prepared by introducing the nucleic acid of the present invention or the recombinant DNA of the present or the carrier for introducing into a cell of the present invention into an appropriate host. The above-mentioned transformant is a transformant harboring the nucleic acid of the present invention or the recombinant DNA of the present invention, and encompassed in the present invention.

The host used includes, for instance, bacteria (for instance, HB101 strain, C600 strain, JM109 strain, and the like of the *Escherichia coli* K-12 derivative); yeast (*Saccharomyces cerevisiae* and the like); microorganisms such as filamentous fungi; cultured cells of mammals (L, 3T3, FM3A, CHO, COS, Vero, Hela, and the like); cultured cells of plants, cultured cells of insects (sf9 and the like) and the like.

In addition, as the method for introducing the recombinant DNA into a host, known methods for introduction can be used. The method for introduction includes, for instance, calcium phosphate method, DEAE-dextran method, electroporation method, and the like.

According to the above-mentioned transformant, there is provided a method for preparing a polypeptide possessing a sphingolipid ceramide deacylase activity. The method for preparing a polypeptide possessing a sphingolipid ceramide deacylase activity is also encompassed in the present invention.

One of the significant features of the method for preparing a polypeptide possessing a sphingolipid ceramide deacylase activity of the present invention resides in that the method comprises the steps of culturing the above-mentioned transformant under conditions appropriate for expression of the sphingolipid ceramide deacylase, and then collecting the polypeptide possessing a sphingolipid ceramide deacylase activity from the resulting culture. In particular, since the transformant of the present invention is used, a polypeptide possessing a sphingolipid ceramide deacylase activity can be obtained efficiently in a large scale. Also, since SCDase is specifically expressed in a heterogeneous host using an expression vector, there are exhibited excellent effects such that inducers for SCDase production (gangliosides such as asialo-GM1) would not be required in the expression of SCDase, that proteins other than SCDase, such as sphingomyelinase, would not be produced simultaneously, and that fatty acids derived from the medium or fatty acids derived from the inducer would not be produced, so that purification is facilitated, as compared to, for instance, the case of *Pseudomonas* sp. TK-4 [Japanese Patent Laid-Open No. Hei 8-84547; *Journal of Biological Chemistry*, 270(41), 24370–24374 (1995)].

In the method of the present invention, when the transformant is a microorganism or a cultured cell, the polypeptide possessing a sphingolipid ceramide deacylase activity can be efficiently prepared by determining operable conditions for expression of the sphingolipid ceramide deacylase of the amount of the inducer used, the time period of its use, and the like, as well as the composition of the culture medium, pH of culture medium, the culturing temperature, and the culturing time.

An ordinary method is employed to purify a polypeptide possessing a sphingolipid ceramide deacylase activity from a culture of the transformant. When the transformant is such that a polypeptide possessing a sphingolipid ceramide deacylase activity is accumulated in cells like in *Escherichia coli*, the transformants are harvested by centrifugation after the termination of cultivation, and the cells obtained are disrupted by ultrasonication or the like, followed by centrifugation or the like, to give a cell-free extract. Using this extract as a starting material, purification can be carried out by ordinary protein purification methods such as ion exchange, gel filtration, hydrophobicity, affinity and other various chromatographies, as well as salting-out. The expression product may be secreted extracellularly depending on the transformant used. In such a case, the expression product may be purified from the culture supernatant in the same manner.

In the polypeptide possessing a sphingolipid ceramide deacylase activity produced by the transformant, there may coexist intracellular enzymes and proteins when produced in cells. However, these enzymes and proteins are present only in trace amounts as compared to the amount of the sphingolipid ceramide deacylase expressed so that there is an advantage that the purification of the polypeptide is highly facilitated. When a vector of the extracellular secretion type is used as the vector, the sphingolipid ceramide deacylase is secreted extracellularly, so that ingredients in the culture medium and the like coexist in the fraction containing the sphingolipid ceramide deacylase. However, since these substances contain almost no protein ingredients that would usually hamper the purification of the sphingolipid ceramide deacylase, there is an advantage such that complicated procedures for separation and purification, which had been required to purify the sphingolipid ceramide deacylase from the culture of the *Shewanella alga* G8 strain, are not necessitated.

In addition, for instance, when the host is *Escherichia coli*, the expression product may be formed as an insoluble inclusion body. In this case, insoluble fractions containing the inclusion bodies are harvested by collecting cells after the termination of cultivation by centrifugation, disrupting the collected cells by ultrasonication or the like, and thereafter carrying out centrifugation or the like. After washing the inclusion bodies, a preparation containing a polypeptide possessing a sphingolipid ceramide deacylase activity can be obtained by solubilizing the inclusion bodies with a commonly used agent for solubilizing a protein, for instance, urea, guanidine hydrochloride, or the like, and, if necessary, purifying the resulting product by various chromatographies such as ion exchange, gel filtration, hydrophobicity and affinity, and thereafter carrying out refolding procedures using dialysis method, dilution method or the like. If this preparation is further purified by various chromatographies as necessary, a high-purity polypeptide possessing a sphingolipid ceramide deacylase activity can be obtained.

The confirmation of expression of the sphingolipid ceramide deacylase can be carried out by determining a sphingolipid ceramide deacylase activity. The determination of the activity can be carried out by, for instance, the method described in *Journal of Biological Chemistry*, 270, 24370–24374 (1995) by using a cell extract of the transformant as a sample. Also, an antibody against the sphingolipid ceramide deacylase can be used. When the sphingolipid ceramide deacylase is expressed as a fusion with another polypeptide, an antibody against the other polypeptide moiety may be used. When an antibody is used, for instance, the cell extract of the transformant is electrophoresed on SDS-polyacrylamide gel and then transferred onto a polyvinylidene fluoride (PVDF) membrane, whereby the sphingolipid ceramide deacylase activity can be detected on this membrane using the antibody.

Furthermore, there is provided an oligonucleotide probe or primer, each being capable of specifically detecting the sphingosine lipid ceramide deacylase gene, according to the nucleic acid of the present invention. The above-mentioned oligonucleotide probe or primer may be those capable of hybridizing to the nucleic acid of the present invention or a nucleic acid complementary thereto under stringent conditions. Here, the stringent conditions may be the "stringent conditions during the oligonucleotide probe" described above.

Also, a sequence suitable for the above-mentioned oligonucleotide probe or primer can be obtained using known software, for instance, Oligo Primer Analysis Software (manufactured by Takara Shuzo Co., Ltd.) or the like, in consideration of the secondary structure formation, Tm value, the specificity to the nucleic acid of the present invention, and the like.

The above-mentioned oligonucleotide probe can be designed on the basis of the nucleotide sequence of the sphingolipid ceramide deacylase gene of the present invention, and can, for instance, be chemically synthesized by a conventional method.

The strand length of the above-mentioned oligonucleotide probe is not particularly subject to limitation. It is preferable that the strand length is at least 15 continuous nucleotides, namely preferably 15 continuous nucleotides or more, more preferably 18 continuous nucleotides or more, from the viewpoint of prevention of nonspecific hybridization.

In addition, the primer of the present invention includes a nucleic acid having the same nucleotide sequence as the above-mentioned oligonucleotide probe. For instance, the primer can be prepared by designing it on the basis of the nucleotide sequence of the gene of the present invention and chemically synthesizing it. The strand length of the primer is not particularly subject to limitation. The primer having a strand length of at least 15 continuous nucleobases, concretely 15 to 40 continuous nucleotides can be used, and a primer having a strand length of 17 to 30 nucleotides can be especially preferably used. The above-mentioned primer can be used for various gene amplification methods such as PCR methods, whereby having an excellent characteristic such that the detection of the sphingolipid ceramide deacylase gene of the present invention can be specifically carried out.

As the above-mentioned oligonucleotide probe or primer, there may also be used a nucleic acid obtained by fragmenting a nucleic acid encoding a naturally occurring sphingolipid ceramide deacylase by an enzymatic treatment such as restriction endonuclease treatment or exonuclease treatment, a physical treatment such as ultrasonication, or the like, and separating and purifying the resulting fragment by various means of nucleic acid separation represented by agarose gel or the like. It is desired that the nucleic acid obtained as described above is derived from a region having a sequence characteristic of the sphingolipid ceramide deacylase.

The above-mentioned oligonucleotide probe or primer can be used for the detection of the sphingolipid ceramide deacylase gene of the present invention by providing appropriate labeling by a commonly known method. The labels are not particularly limited, and there can be used fluorescent substances, ligands such as biotin and digoxigenin, as well as radioisotopes.

There is provided a method for detecting a nucleic acid encoding a polypeptide possessing a sphingolipid ceramide deacylase activity, according to the oligonucleotide probe or the primer of the present invention. One of the significant features of the detection method of the present invention resides in the use of the above-mentioned oligonucleotide probe and/or primer, whereby the gene in a sample to be tested is detected. More concretely, the detection method includes a method comprising contacting a sample to be tested containing a nucleic acid with the oligonucleotide probe of the present invention, and thereafter detecting a hybrid of the nucleic acid with the oligonucleotide probe, or a method comprising carrying out nucleic acid amplification using the primer of the present invention with the sample to be tested containing a nucleic acid as a template sample.

In the detection method of the present invention, the gene may be detected by carrying out hybridization or the like under stringent conditions using the above-mentioned oligonucleotide probe. Alternatively, the gene may be detected by a DNA amplification method such as PCR method using the above-mentioned primer. Also, both the methods may be used in combination.

When the oligonucleotide probe is used, the sample to be tested includes, for instance, samples such as those of microbial colonies and tissue fragments, those in which DNA or RNA in these samples is immobilized on a membrane, DNA and RNA extracted from these samples, and the like. Among them, those in which DNA is immobilized on a membrane or DNA extracted are especially preferred, from the viewpoint of stability of the samples.

When the oligonucleotide probe is used, the gene can be detected by carrying out hybridization under the above-mentioned stringent conditions.

When a primer is used, the sample to be tested includes, for instance, microbial samples such as microbial culture media, microbial colonies, and microbial cells, and biological samples such as skin, tissue, and tissue fragments.

When the above-mentioned primer are used, as the sample to be tested, for instance, an isolated microorganism may be directly used, or an isolated microorganism may be used after an appropriate treatment. Also, regarding solid samples such as tissues, exudates or suspensions can be prepared to be used. In addition, there can be used samples obtained by cytolytic treatment such as surfactant treatment of supernatants of these samples or these samples, and supernatants thereof. Furthermore, procedures for removing other ingredients in the sample may be carried out, as long as the nucleic acid to be detected is not impaired.

When the detection is carried out by PCR method using the above-mentioned primers, PCR conditions can be selected as appropriate according to the Tm value of the primer used, the length of the region to be amplified and detected, and the like.

When the above-mentioned primers are used, the nucleic acid can be detected by carrying out amplification by a DNA amplification method such as PCR method, and confirming the presence or absence of a PCR amplification product. The method of confirming the presence or absence of amplification is not particularly limited. For instance, the amplification can be confirmed by subjecting a reaction mixture for nucleic acid amplification to agarose gel electrophoresis, thereafter staining the gel with an appropriate nucleic acid staining reagent, for instance, ethidium bromide, SYBER Green I, or the like, and detecting the presence or absence of the band formed by irradiation with ultraviolet rays. Although the band can be observed by macroscopic observation, the band can also be detected using, for instance, a fluorescence image analyzer or the like.

In the detection method of the present invention, the above-mentioned probe and primer may be used in combination to increase the detection sensitivity. For instance, highly sensitive and accurate detection can be achieved by amplifying a sphingolipid ceramide deacylase gene existing in a trace amount in the sample by PCR method using the above-mentioned primer, and subsequently hybridizing the amplification product to the gene using the probe.

When the sphingolipid ceramide deacylase gene is detected and the expression level of the gene is further determined by the detection method of the present invention, there can be carried out quantification of the intensity of the signal from the probe hybridized under stringent conditions, the fluorescence intensity of the band ascribed to the product amplified using a primer, and the like.

One of the features of the kit of the present invention usable for the method for detecting a nucleic acid resides in that the kit comprises the above-mentioned oligonucleotide probe and/or primer.

The kit of the present invention may further comprise a membrane for immobilizing the nucleic acid, various hybridization reagents represented by hybridization buffers or the like, a thermostable DNA polymerase, a dNTP mixture, PCR reagents represented by PCR buffers, a probe, reagents for detecting amplified DNA, a medium for proliferating microbes, a reagent for extracting a nucleic acid from the sample, and the like.

Also, according to the polypeptide of the present invention, or the polypeptide obtained by expressing the nucleic acid of the present invention, there is provided antibody or a fragment thereof capable of specifically binding to the above polypeptide. The antibody or a fragment thereof is also encompassed in the present invention.

The antibody or a fragment thereof of the present invention is not particularly limited, as long as the antibody or a fragment thereof possesses an ability of specifically binding to the polypeptide. The antibody may be any of polyclonal antibodies and monoclonal antibodies. Further, antibodies modified by known techniques or antibody derivatives, for instance, humanized antibodies, Fab fragments, single-chain antibodies, and the like, can also be used. The antibody of the present invention can be readily prepared by appropriately immunizing a rabbit, a mouse or the like using all or a part of the polypeptide of the present invention in accordance with the method described in, for instance, *Current Protocols in Immunology*, edited by John E. Coligan, published by John Weily & Sons, Inc., 1992. In addition, the antibody can be prepared by genetically engineering means. Also, there is included an antibody or a fragment thereof capable of specifically binding to a given partial fragment of the polypeptide.

Further, the resulting antibody is purified, and thereafter treated with peptidase or the like, to give an antibody fragment. The applications of the resulting antibody or a fragment thereof include detection of sphingolipid ceramide deacylase-producing bacteria, affinity chromatography, screening of an expression product of various kinds of libraries (genomic DNA or cDNA), pharmaceuticals, diagnostic agents, reagents for researches, and the like.

In addition, the antibody or a fragment thereof of the present invention may be subjected to various modifications in order to facilitate the detection by enzyme immunoassay, fluoroimmunoassay, luminescent immunoassay, or the like.

The method for detecting a polypeptide of the present invention is characterized by the use of the above-mentioned antibody or a fragment thereof, whereby a polypeptide possessing a sphingolipid ceramide deacylase activity is detected. Concretely, a sample to be tested containing a polypeptide is contacted with the above-mentioned antibody or a fragment thereof, and a complex of the polypeptide with the antibody or a fragment thereof is detected.

In the present invention, the samples to be tested include, for instance, microbial cell disruptions, extract or washings of tissues such as skin, and protein samples such as membranes immobilized with tissue-derived or microorganism-derived protein.

As the detection of a specific binding of an antibody or a fragment thereof to the above-mentioned polypeptide, there can be utilized various known methods. For instance, there are included enzyme immunoassay, fluoroimmunoassay, luminescent immunoassay, or the like.

One of the features of the kit usable for the method for detecting a polypeptide of the present invention resides in that the kit comprises the above-mentioned antibody or a fragment thereof. According to the kit of the present invention, since the kit comprises the above-mentioned antibody or a fragment thereof, a polypeptide possessing a sphingolipid ceramide deacylase activity can be detected specifically and conveniently.

The kit of the present invention may further comprise a reaction buffer, a labeled secondary antibody, a developing reagent, or the like.

Furthermore, according to the nucleic acid of the present invention, there can be achieved applications for the treatment of diseases associated with sphingolipid metabolism, for instance, diseases of nervous system (for instance, neurodegenerative diseases and the like), leukemia, wounds, and the like. Hence, there can be provided a therapeutic agent for diseases associated with sphingolipid metabolism, concretely diseases of nervous system (for instance, neurodegenerative diseases and the like), leukemia, wounds, and the like, comprising the nucleic acid of the present invention as an effective ingredient, and use of the nucleic acid of the present invention for the treatment of diseases associated with sphingolipid metabolism, concretely the above-mentioned diseases of nervous system, leukemia, wounds, and the like.

The above-mentioned therapeutic agent may be an agent obtained by allowing a carrier capable of stably maintaining the above-mentioned effective ingredient to carry the effective ingredient, and includes, for instance, the above-mentioned carrier for introducing into cells. Concretely, for instance, a pharmaceutically acceptable carrier capable of facilitating introduction into an individual, a living body such as an organ, a local site, or a tissue which is to be administered may be allowed to carry the effective ingredient. In addition, the therapeutic agent may further comprise other auxiliaries according to the condition or disease for which administration of the therapeutic agent is required [for instance, diseases of nervous system (for instance, neurodegenerative diseases and the like), leukemia, wounds, and the like]; the individual, organ, local site, or tissue, which is to be administered. Concretely, a pharmacologically acceptable auxiliary exhibiting a characteristic of suppressing the decomposition of the nucleic acid until the agent reaches the site where the effects of the effective ingredient are exhibited, an excipient, a binder, a stabilizer, a buffer, a dissolution aid, an isotonic agent, or the like may also be contained. The content of the effective ingredient can be selected as appropriate according to the condition or disease for which administration of the agent is required; the individual, organ, local site, or tissue, which is to be administered; the age of the individual to be administered, and the like.

The dosage forms for the above-mentioned therapeutic agent include topical administration, subcutaneous injection, intramuscular injection, intravenous injection, and the like.

When the nucleic acid of the present invention is used in the treatment of diseases associated with metabolism of the sphingolipids, concretely the above-mentioned diseases of nervous system, leukemia, wounds, and the like, there may be carried out, for instance, a method comprising introducing directly into a body a therapeutic agent obtained by allowing a carrier suitable for introduction into cells, such as a viral vector or liposome, to carry the nucleic acid, or a method comprising introducing extracorporeally a therapeutic agent into a certain kind of cells from an animal, for instance, a mammal, and returning the cells obtained to the body.

The present invention is hereinafter concretely described by means of the following examples, without intending to limit the scope of the present invention thereto.

EXAMPLE 1

Screening of Microorganisms Producing Sphingolipid Ceramide Deacylase

Samples (seawater, river water, or body surfaces or gastrointestinal tracts of organisms living therein) were collected from various places, and suspended in sterile physiological saline. Ten microliters of the suspension obtained was inoculated to 400 µl of a liquid medium containing 0.01% ceramide, 0.05% $NH_4Cl$, 0.05% $K_2HPO_4$, 0.1% yeast extract, 2.0% NaCl, and 0.01% TDC, pH 7.0 in an Eppendorf tube, and cultured with shaking at 25° C. for 4 days. Thereafter, the sphingolipid ceramide deacylase (hereinafter also referred to as SCDase) activity was determined, and an active culture medium was selected.

The SCDase activity of the above-mentioned culture medium was determined using NBD-GM1 as a substrate. NBD-GM1, GM1 of which fatty acid moiety of ceramide is labeled with NBD (7-nitrobenz-2-oxa-1,3-diazol-4-yl), was prepared by the method described in *Journal of Biochemistry*, 126, 604–611 (1999).

Here, the activity was determined as described below. Concretely, 10 µl of an enzyme solution was added to 10 µl of a 50 mM acetate buffer (pH 6.0) containing 0.1% Triton X-100 and 100 pmol of NBD-GM1, and incubated at 37° C. for a given time. Thereafter, the solution was boiled at 100° C. for 5 minutes to stop the reaction, and the reaction mixture was completely dried by using SPEEDVAC concentrator. Fifteen microliters of chloroform/methanol (2:1, v/v) was added thereto, and the reaction product was dissolved by sonication. The solution obtained was spotted onto a silica gel TLC plate. After development with chloroform/methanol/0.2% $CaCl_2$ (5:4:1, v/v), the degradation ratio was determined using the SHIMADZU CS-9300 chromatoscan ner (absorbance at 475 nm). Furthermore, the degradation ratio was calculated using the equation:

Degradation Ratio (%)=[Area of Liberated lyso-GM1×100]/[Area of Liberated Lyso-GM1+Area of Unreacted GM1].

One unit (U) was defined as an amount of enzyme for degrading 1 μmol of NBD-GM1 per minute.

The culture medium thus selected was diluted with sterile physiological saline, and the dilution obtained was plated to a plate medium. After plating, the plate medium was cultured at 25° C. for 2 days to form colonies. A series of these procedures were repeated until a single colony was obtained. As a result, *Shewanella alga* G8 strain producing a sphingolipid ceramide deacylase was isolated from a sample collected from sea sand of Konagai-cho, Nagasaki Prefecture.

EXAMPLE 2

Cloning of Structural Gene for Sphingolipid Ceramide Deacylase (1) Extraction and Purification of Genomic DNA

*Shewanella alga* G8 strain, a microorganism producing sphingolipid ceramide deacylase, was inoculated to 200 ml of PY medium (0.5% polypeptone, 0.1% yeast extract, 0.5% sodium chloride, pH 7.2) and cultured at 25° C. for 22 hours. After the termination of the cultivation, the culture medium obtained was centrifuged to harvested the cells, and the cells were suspended in 10 ml of TE buffer (10 mM Tris-HCl, 1 mM EDTA, pH 8.0). The amount 0.2 ml of a 50 mg/ml egg white lysozyme solution was further added to the suspension obtained, and the reaction was carried out at 30° C. for 15 minutes. Next, 2 ml of 10% SDS was added to the solution obtained after the termination of the reaction, and the mixture was gently stirred. When the solution became viscous, 10 ml of TE buffer-saturated phenol and 1.5 ml of 5 M NaCl were immediately added thereto, and the mixture was gently stirred at room temperature for 1 hour. The solution obtained after stirring was centrifuged at 2500 rpm for 10 minutes, and thereafter the upper layer was collected. An equal volume of chloroform was added to the upper layer obtained, and the mixture was stirred for 10 minutes, and thereafter centrifuged at 1500 rpm for 10 minutes to collect the upper layer. An equal volume of chloroform was again added to the upper layer obtained, with stirring, and thereafter the mixture was centrifuged to collect the upper layer (a series of the procedures are hereinafter referred to as phenol-chloroform treatment). An equal volume of isopropanol was gradually added to the collected solution. The DNA precipitated in the interface was taken with a Pasteur pipette and dissolved in 10 ml of TE buffer. Twenty microliters of RNase A (those obtained by dissolving RNase A so as to have a concentration of 10 mg/ml in 10 mM Tris-HCl, pH 7.5, 15 mM NaCl, and heat-treated at 100° C. for 15 minutes) was added to the solution obtained, and the mixture was incubated at 50° C. for 1 hour. Ten microliters of a 20 mg/ml protease K solution, 200 μl of 5 M NaCl, and 400 μl of 10% SDS were further added to the solution obtained after incubation, and the mixture was incubated at 37° C. for 1 hour to carry out the reaction. The solution obtained after the reaction was cooled to room temperature and treated with phenol-chloroform. The above procedures were repeated twice. An equal volume of isopropanol and a 1/10 volume of 3 M sodium acetate were added to the aqueous layer obtained, and the mixture was cooled at −20° C. for 1 hour, and thereafter centrifuged at 10000 rpm for 10 minutes to give precipitates. The precipitates obtained were rinsed with 70% ethanol and dissolved in TE buffer to give a genomic DNA solution. By the procedures, 1.1 mg of genomic DNA was obtained.

(2) Determination of Partial Amino Acid Sequences of Sphingolipid Ceramide Deacylase The sphingolipid ceramide deacylase produced by *Shewanella alga* G8 strain was purified. *Shewanella alga* G8 strain was cultured in a medium containing 0.5% polypeptone, 0.1% yeast extract, 2% NaCl, and 0.1% bovine brain acetone powder at 25° C. for 22 hours. After the termination of the cultivation, the culture medium was centrifuged at 8300 rpm for 30 minutes to give 4.6 liters of culture supernatant. The SCDase activity in this culture supernatant was 55.5 units (U). One unit (U) of the SCDase activity was defined as an amount of enzyme for degrading 1 μmol of GM1 per minute.

The culture supernatant obtained was concentrated up to 1 liter through an ultrafiltration membrane having an excluding molecular weight of 10000 using the Minitan ultrafiltration system (manufactured by Millipore Corporation), and subjected to column chromatography (bed volume 80 ml) on Butyl-Toyopearl 650 M. The concentrated culture supernatant was applied to the column which had been previously equilibrated with a 20 mM Tris-HCl buffer (pH 7.5) containing 2 M sodium chloride. Next, the column was washed with 20 mM Tris-HCl buffer (pH 7.5), and thereafter the adsorbed SCDase was eluted with a 20 mM Tris-HCl buffer (pH 7.5) containing 2% Lubrol PX (manufactured by nakalai tesque).

The active fraction was collected to give 17.7 U of SCDase.

Next, this active fraction was applied to a column (30 ml) of DEAE-Sepharose (manufactured by Amersham Pharmacia Biotech) which had been previously equilibrated with a 20 mM Tris-HCl buffer (pH 7.5) containing 0.1% Lubrol PX. The column was sufficiently washed with the above-mentioned equilibration buffer, and thereafter the adsorbed enzyme was eluted with a 20 mM Tris-HCl buffer (pH 7.5) containing 1 M sodium chloride and 0.1% Lubrol PX.

The active fraction was collected to give 13.5 U of SCDase.

As a result of analysis for this fraction by SDS-polyacrylamide gel electrophoresis, a band of SCDase was detected at a position corresponding to a molecular weight of 75000.

By the purification method described above, 13.5 U of SCDase, purified 1600 folds, was finally obtained in a yield of 24%.

About 5 μg of the SCDase obtained was subjected to SDS-polyacrylamide gel electrophoresis, and then electrophoresed. Subsequently, the protein on the gel was transferred to a PVDF membrane (Immobilon-P, manufactured by Millipore Corporation) by electroblotting method. The portion (about 50 pmol) corresponding to the SCDase band of this membrane was cut out, and thereafter incubated at 37° C. for 16 hours with shaking the portion in 100 μl of a 20 mM Tris-HCl buffer containing 0.2 mg of lysylendopeptidase (0.9 U) and 8% acetonitrile, to thereby enzymatically digest the SCDase.

This enzyme digest was subjected to reverse-phase chromatography to carry out purification of the peptide fragment. The peptide fragment obtained was analyzed according to the Edman degradation method by using Model 477 gas phase peptide sequencer (manufactured by Applied Biosystems Ltd.) to determine internal partial amino acid sequences C-606 (SEQ ID NO: 3), C-599 (SEQ ID NO: 4), C-614 (SEQ ID NO: 5), and C-616 (SEQ ID NO: 6) of SCDase.

Also, separately from above, the above-mentioned PVDF membrane was subjected to a peptide sequencer without lysylendopeptidase treatment, to determine the N-terminal amino acid sequence C-603 (SEQ ID NO: 7).

(3) Amplification by PCR Method of DNA Fragment Containing Sphingolipid Ceramide Deacylase Gene Primers were designed according to the N-terminal amino acid sequence and the internal partial amino acid sequences determined in item (2) of Example 2 of sphingolipid ceramide deacylase, and synthesized using a DNA synthesizer.

Concretely, each of sense mix primer SS1 (SEQ ID NO: 8), sense mix primer SS2a (SEQ ID NO: 9) and sense mix primer SS2b (SEQ ID NO: 10), corresponding to C-603 shown in SEQ ID NO: 7, was synthesized, and each of antisense mix primer SA1a (SEQ ID NO: 11), antisense mix primer SA1b (SEQ ID NO: 12) and antisense mix primer SA3 (SEQ ID NO: 13), corresponding to C-606 shown in SEQ ID NO: 3, was synthesized.

PCR was carried out using these primers. In the PCR, 35 cycles of reaction was carried out, wherein one cycle comprises 95° C. for 0.3 minutes, 52° C. for 0.5 minutes, and 72° C. for 1.5 minutes, using AmpliTaq Gold (manufactured by PE Biosystems) in accordance with the attached protocol.

PCR was carried out by each of combinations of primer SS2a and primer SA3; SS1 and SA1a; SS1 and SA1b; SS1 and SA3; SS2a and SA1a; SS2a and SA1b; SS2b and SA1a; SS2b and SA1b; and SS2b and SA3, with the genomic DNA from *Shewanella alga* G8 strain obtained in item (1) of Example 2 as a template. As a result, amplification of a specific band corresponding to about 1000 bp was detected.

An amplified DNA fragment of about 1000 bp mentioned above was collected from the gel after agarose gel electrophoresis. The DNA fragment obtained was ligated to pGEM-T easy vector (manufactured by Promega) to thereby construct a recombinant plasmid. The nucleotide sequence of the amplified DNA fragment mentioned above was determined by the dideoxy method with the plasmid as a template.

As a result, the nucleotide sequences each encoding the N-terminal amino acid sequence C-603 and partial amino acid sequences C-606 and C-599 of the sphingolipid ceramide deacylase were found in the nucleotide sequence obtained, clarifying that this amplified DNA fragment is a part of the desired gene encoding the sphingolipid ceramide deacylase.

(4) Detection of DNA Fragment Containing Sphingolipid Ceramide Deacylase Gene

Screening for genomic DNA fragments containing the SCDase gene was carried out, using the PCR-amplified DNA fragment obtained in item (3) of Example 2 as a probe.

First, 51 g of the genomic DNA prepared in item (1) of Example 2 was digested at 37° C. for 22 hours using 100 units each of the restriction endonucleases ApaI, KpnI, SalI, EcoRV, BamHI, XbaI and SacI. The restriction endonuclease-digested DNA obtained was subjected to 1% agarose gel electrophoresis. After the electrophoresis, the DNA was transferred onto a nylon membrane [Hybond-N+, manufactured by Amersham Pharmacia Biotech] by the Southern blot technique. As the hybridization probe, there was used one in which 0.1 μg of the PCR-amplified DNA fragment obtained in item (3) of Example 2 was labeled with $^{32}$p in accordance with the protocol attached to a DNA labeling kit [ReadyTo Go, manufactured by Amersham Pharmacia Biotech].

Pre-hybridization of the nylon membrane mentioned above was carried out in a hybridization solution containing a 0.5 M Church method phosphate buffer [*Proceedings of the National Academy of Sciences of the USA*, 81, 1991–1995 (1984)] pH 7.0, 7% SDS, and 1 mM EDTA at 65° C. for 1 hour or more. Next, the above-mentioned labeled probe was added thereto so as to have a concentration of 6 fmol/ml, and hybridization was carried out overnight at 65° C.

Next, washing in a washing solution (1% SDS, 40 mM sodium phosphate buffer) which had been previously heated to 65° C., was repeated thrice at 65° C. for 15 minutes. After excess water was removed, the nylon membrane was photosensitized by contact with the FUJI PHOTO FILM imaging plate (manufactured by Fuji Photo Film Co., Ltd.) for 20 minutes. After photosensitization, the imaging plate was analyzed using the BAS1000 imaging analyzer (manufactured by Fuji Photo Film Co., Ltd.) to detect the probe on the nylon membrane. As a result, in each of the ApaI, KpnI, SalI, EcoRV, BamHI, XbaI and SacI digests, a signal ascribed to the hybridized probe was detected at positions corresponding to about 10 kb, about 5 kb, about 2.3 kb, about 4.4 kb, about 10 kb, about 10 kb, and about 4 kb, respectively.

(5) Cloning of Sphingolipid Ceramide Deacylase Gene

On the basis of the results of item (4) of Example 2, the EcoRV fragment of about 4.4 kb was cloned. Ten milligrams of EcoRV-digested genomic DNA was separated by 1% agarose gel electrophoresis, and the agarose gel at a position corresponding to a size of about 4.4 kb was cut out. A DNA fragment was extracted and purified from the gel using the Sephaglas BandPrep Kit (manufactured by Amersham Pharmacia Biotech), and this DNA fragment was inserted into EcoRV site of pBluescript II SK (manufactured by TOYOBO CO., LTD.) to thereby construct a recombinant plasmid. *Escherichia coli* JM109 was transformed with the above-mentioned plasmid. Next, 300 colonies were selected from the colonies that appeared after overnight cultivation on an L agar medium (1% trypton, 0.5% yeast extract, 1% NaCl, pH 7.2, 1% agar) plate containing 100 μg/ml ampicillin, and inoculated onto a nylon membrane [Hybond-N, manufactured by Amersham Pharmacia Biotech] placed on the same plate medium. After cultivation at 37° C. for 16 hours, this nylon membrane was treated for 5 minutes (denaturation) on filter paper immersed in an alkali denaturing solution (0.5 M NaOH, 1.5 M NaCl) and for 5 minutes (neutralization) on filter paper immersed in a neutralizing solution (0.5 M Tris-HCl (pH 7.5), 3 M NaCl). Thereafter, the treated product was rinsed with 2×SSC (1×SSC composition: 0.15 M NaCl, 0.015 M sodium citrate, pH 7.0).

Hybridization of this nylon membrane was carried out under the same conditions as those described above using the PCR-amplified DNA fragment obtained in item (3) of Example 2 as a probe. As a result, a signal was obtained for two colonies. A plasmid was prepared from one of these colonies and named as pSCD1, and the nucleotide sequence of the DNA insert of this plasmid was determined. As a result, a stop codon was found in the same frame for each of sequences corresponding to the amino acid sequences C-606, C-599, C-614, and C-616 and N-terminal amino acid sequence C-603 obtained in item (2) of Example 2. Hence, this plasmid was clarified to contain the full-length SCDase gene consisting of a 2976 bp open reading frame. The *Escherichia coli* JM109 transformed with this plasmid pSCD44 was named and identified as *Escherichia coli* JM109/pSE5 and transferred from the original deposit to that under the Budapest Treaty with the accession number of FERM BP-7717 with the International Patent Organism Depositary, National Institute of Advanced Industrial Science and Technology, of which the address is AIST Tsukuba Central 6, 1-1, Higashi 1-chome, Tsukuba-shi, Ibaraki-ken 305-8566, Japan, since Aug. 24, 2001 (original date of deposit: Sep. 22, 2000).

The restriction map of the DNA insert in the plasmid pSCD1 is shown in FIG. 1. From the analytical results for the nucleotide sequence of this plasmid, the entire nucleotide sequence of the sphingolipid ceramide deacylase gene and the amino acid sequence of sphingolipid ceramide deacylase were determined. The nucleotide sequence of the open reading frame (ORF) encoding the SCDase produced by *Shewanella alga* G8 strain is shown in SEQ ID NO: 14, and the amino acid sequence encoded by this ORF is shown in SEQ ID NO: 15, respectively.

The nucleotide sequence encoding mature SCDase, which was clarified from the N-terminal amino acid sequence C-603 (SEQ ID NO: 7) of the sphingolipid ceramide deacylase obtained in item (2) of Example 2, is shown in SEQ ID NO: 2, and the amino acid sequence of mature SCDase encoded by this nucleotide sequence is shown in SEQ ID NO: 1.

EXAMPLE 3

Construction of Plasmid Expressing Sphingolipid Ceramide Deacylase Polypeptide

A plasmid expressing the sphingolipid ceramide deacylase was constructed according to the procedures described below.

Each of primer UN1 (SEQ ID NO: 16) in which NheI site was added and primer LC1 (SEQ ID NO: 17) in which XhoI site was added was synthesized on the basis of each of the N-terminal and C-terminal nucleotide sequences of the sphingolipid ceramide deacylase. PCR was carried out using these primers, with the plasmid pSCD1 described in Example 2 above as a template. In the PCR, 25 cycles of reaction was carried out, wherein one cycle comprises 98° C. for 10 seconds and 68° C. for 3.5 minutes, using Pyrobest DNA polymerase (manufactured by Takara Shuzo Co., Ltd.) in accordance with the attached protocol. As a result of PCR under the conditions described above, amplification of an about 3 kb specific band was detected.

This amplified DNA fragment of about 3 kb was collected from the gel after agarose gel electrophoresis and digested with restriction endonucleases NheI and XhoI. The fragment obtained was ligated to pET23a vector (manufactured by Novagen) to give recombinant plasmid pSCD2.

EXAMPLE 4

Expression of Sphingolipid Ceramide Deacylase in Transformed *Escherichia coli*

*Escherichia coli* BL21pLysS (manufactured by Novagen) was transformed with the plasmid pSCD2 obtained in Example 3, to give *Escherichia coli* BL21/pSCD2. The transformant was inoculated to 3 ml of an LB medium containing 100 μg/ml ampicillin and cultured overnight with shaking at 37° C. Next, 0.5 ml of the culture medium obtained was inoculated to 50 ml of the same medium. Thereafter, cultivation was carried out at 37° C. At the stage where the turbidity (absorbance at 600 nm) reached about 0.5, isopropyl-β-D-thiogalactoside (IPTG) was added so as to have a final concentration of 0.1 mM, and cultivation was carried out with shaking at 37° C. for 30 minutes. After the termination of the cultivation, the culture medium was centrifuged to harvest the cells, and the cells were suspended in a 50 mM acetate buffer (pH 6.0) containing 5 ml of 0.1% Triton X-100 and 0.8 M NaCl. Thereafter, ultrasonication treatment was carried out to disrupt the cells. The disruption obtained was centrifuged, to collect the supernatant to give a crude enzyme solution.

The SCDase activity of this crude enzyme solution was determined using NBD-GM1 as a substrate in the same manner as in Example 1 described above. As a result, it was shown that *Escherichia coli* BL21pLysS/pSCD2 harboring the sphingolipid ceramide deacylase gene of the present invention produced about 1 U of sphingolipid ceramide deacylase per one liter of the culture medium.

EXAMPLE 5

Construction of Kit Usable for Detecting of Nucleic Acid Encoding Polypeptide Possessing Sphingolipid Ceramide Deacylase Activity An oligonucleotide probe and primers were prepared on the basis of the nucleotide sequence shown in SEQ ID NO: 2, and the following kit usable for detecting a nucleic acid encoding a polypeptide possessing a sphingolipid ceramide deacylase activity was constructed.

This kit comprises a set of primers capable of amplifying a region specific to the sphingolipid ceramide deacylase, a DNA polymerase, a PCR buffer, and a dNTP mixture.

The probe specific to the amplified region for carrying out hybridization after amplification is included in the kit where necessary.

For instance, the kit as described below was prepared.

| Constitution of Kit (100 Runs of PCR) | |
|---|---|
| SS1 (20 pmol/μl) | 110 μl |
| SS2a (20 pmol/μl) | 110 μl |
| SS2b (20 pmol/μl) | 110 μl |
| SA1a (20 pmol/μl) | 110 μl |
| SA1b (20 pmol/μl) | 110 μl |
| SA3 (20 pmol/μl) | 110 μl |
| 10 × PCR Buffer | 1 ml |
| TaKaRa Taq (5 U/μl) | 50 μl |
| dNTP Mixture (2.5 mM each) | 1.28 μl |

EXAMPLE 6

Construction of Kit Usable for Detecting Polypeptide Possessing Sphingolipid Ceramide Deacylase Activity A goat, a rabbit, a rat, a mouse, or the like was immunized with a polypeptide having the amino acid sequence shown in SEQ ID NO: 1 as an antigen, thereby preparing an anti-sphingolipid ceramide deacylase antibody, and the following kit usable for detecting a polypeptide possessing a sphingolipid ceramide deacylase activity was constructed.

This kit is a kit for sandwich EIA, comprising a 96-well plate coated with an anti-SCDase monoclonal antibody, a peroxidase-labeled anti-SCDase monoclonal antibody, standard, a solution for dilution, a substrate solution (TMBZ: 3,3',5,5'-tetramethylbenzidine) and a reaction stop solution (1 N sulfuric acid).

For example, the following kit was prepared.

| Constitution of Kit (96 Runs) | |
|---|---|
| Anti-SCDase Monoclonal Antibody Plate (96 wells (8 wells × 12 strips) | 1 sheet |
| Peroxidase-Labeled Anti-SCDase Monoclonal Antibody (Lyophilized Product) | Use for 11 ml × 1 |
| Standard (Lyophilized Product) | Use for 1 ml × 1 |
| Solution for Dilution | 11 ml × 1 |
| Substrate Solution (TMBZ) | 12 ml × 1 |
| Reaction Stop Solution (1 N Sulfuric Acid) | 12 ml × 1 |

EXAMPLE 7

Construction of Plasmid for Expressing Deletion Mutant of Sphingolipid Ceramide Deacylase Polypeptide Which Lacks C-Terminal A plasmid for expressing a deletion mutant of sphingolipid ceramide deacylase which lacks C-terminal was constructed in accordance with the procedures described below.

Primer LSCD2125 (SEQ ID NO: 18) was synthesized on the basis of a nucleotide sequence corresponding to a 75 kDa portion from an N-terminal clarified by the deduced peptide sequence of the purified enzyme, namely a nucleotide sequence corresponding to the C-terminal side (ERAEAH) portion. PCR was carried out using the primer LSCD2125 obtained and the primer UN1 (SEQ ID NO: 16) synthesized in Example 3, with the plasmid pSCD1 described in Example 2 above as a template. The PCR was carried out by 30 cycles of reaction, wherein one cycle comprises 96° C. for 10 seconds and 68° C. for 2.5 minutes using PyroBest DNA polymerase (manufactured by Takara Shuzo Co., Ltd.) in accordance with the attached protocol. As a result of the PCR under the conditions described above, amplification of a specific band of about 2 kb was detected.

The 2 kb amplified DNA fragment obtained was recovered from the gel after agarose gel electrophoresis, and digested with the restriction endonucleases NheI and XhoI to give a fragment encoding SCDase in which a C-terminal region was deleted. The fragment obtained was ligated to pET23b vector (manufactured by Novagen), previously digested with restriction endonucleases NheI and XhoI, to prepare recombinant plasmid pETSCD-del.

The nucleotide sequence of DNA encoding SCDase in which the C-terminal region was deleted is shown in SEQ ID NO: 19, and the amino acid sequence encoded by the above-mentioned nucleotide sequence is shown in SEQ ID NO: 20.

EXAMPLE 8

Expression of Deletion Mutant of Sphingolipid Ceramide Deacylase Which Lacks C-Terminal in Transformant *Escherichia coli*

*Escherichia coli* BL21(DE3)pLysE (manufactured by Novagen) was transformed with the plasmid pETSCD-del obtained in Example 7, to give transformant *Escherichia coli* BL21(DE3)pLysE/pETSCD-del. The transformant was inoculated to 5 ml of an LB medium containing 100 µg/ml ampicillin and 35 µg/ml chloramphenicol, and cultured overnight with shaking at 25° C. Next, the culture medium obtained was inoculated to 1 liter of the same culture medium in a 2-liter baffled flask. Thereafter, the culture obtained was cultured with shaking at 25° C. for 18 hours, and isopropyl-β-D-thiogalactoside (IPTG) was added to the culture medium so as to have a final concentration of 0.1 mM, and the cells were further cultured with shaking at 25° C. for 1 hour. After the termination of the cultivation, the culture medium was centrifuged to collect the cells, and suspended in 50 ml of a 10 mM Tris-HCl buffer (pH 7.5) containing 0.1% Triton X-100, 150 mM NaCl, 1 mM phenylmethanesulfonyl fluoride (PMSF), 5 µg/ml pepstatin, 5 µg/ml chymostatin and 5 µg/ml leupeptin. Subsequently, the suspension obtained was frozen at −80° C. and then thawed to disrupt the cells. Furthermore, the disrupted cells were subjected to ultrasonication to disrupt the cells. The disruption obtained was centrifuged, and the supernatant was collected to give a crude enzyme solution.

The SCDase activity of the crude enzyme solution obtained was determined as described below. Specifically, 101 µl of the crude enzyme solution was added to 10 µl of a substrate solution [10 nmol GM1a, 5 mM $MgCl_2$, 5 mM $MnCl_2$, 5 mM $CaCl_2$, 0.2% Triton X-100, 200 mM NaCl, 50 mM acetate buffer (pH 5.5)], and the mixture was incubated at 37° C. for 30 minutes to react the crude enzyme solution with the substrate. Thereafter, the enzyme solution was boiled at 100° C. for 5 minutes to stop the reaction. The reaction product obtained was concentrated to dryness using a centrifugal concentrator. Ten microliters of chloroform/methanol (2:1, v/v) was added to the product obtained, and the mixture obtained was treated with ultrasonication to dissolve the reaction product. The solution obtained was spotted onto a silica gel TLC plate. After development with chloroform/methanol/0.02% $CaCl_2$ (5:4:1, v/v/v), the glycolipid on the silica gel TLC plate was allowed to develop a color by the orcinol-sulfuric acid method. After color development, the silica gel TLC plate was determined for its absorbance (wavelength: 540 nm) by using a TLC chromatoscanner (manufactured by SHIMADZU CORPORATION), and the degradation ratio was calculated from the following equation:

Degradation Ratio (%)=([Area of Liberated Lyso-*GM*1a]/[Area of Liberated Lyso-*GM*1a+Area of Unreacted *GM*1a])×100

Here, one unit (U) of SCDase (U) was defined as the amount of enzyme for degrading 1 µmol of GM1a per minute.

As a result of the determination of the activity by the method mentioned above, it was shown that *Escherichia coli* BL21(DE3)pLysE/pETSCD-del harboring the gene encoding the deletion mutant of sphingolipid ceramide deacylase which lacks C-terminal of the present invention produced 872 U of deletion mutant of sphingolipid ceramide deacylase which lacks C-terminal per one liter of the culture medium.

A purified SCDase preparation was obtained according to the method as described below.

Concretely, the above-mentioned crude enzyme solution was applied to the HiTrap Chelating column (manufactured by Amersham Pharmacia Biotech) which had been previously equilibrated with a 10 mM Tris-HCl buffer (pH 7.5) containing 0.1% Triton X-100 and 150 mM NaCl. Next, impurity proteins were eluted with a 10 mM Tris-HCl buffer (pH 7.5) containing 20 mM imidazole. Thereafter, the SCDase was eluted with a 10 mM Tris-HCl buffer (pH 7.5) containing 50 mM imidazole to collect an active fraction (1).

The active fraction (1) collected was dialyzed against a 10 mM Tris-HCl buffer (pH 7.5) containing 0.1% Triton X-100. The above-mentioned dialyzate was applied to HiTrap Q column (manufactured by Amersham Pharmacia Biotech) which had been previously equilibrated with a 10 mM Tris-HCl buffer (pH 7.5) containing 0.1% Triton X-100. Next, the SCDase was eluted with a 10 mM Tris-HCl buffer (pH 7.5) containing 0.1% Triton X-100 and 1M NaCl to collect an active fraction (2).

The above-mentioned active fraction (2) was applied to HiLoad Superdex 200 pg column (manufactured by Amersham Pharmacia Biotech) which had been previously equilibrated with a 10 mM Tris-HCl buffer (pH 7.5) containing 0.1% Triton X-100 and 150 mM NaCl. An active fraction (3) that passed through the column without being adsorbed was collected.

The above-mentioned active fraction (3) was applied to HiTrap Q column (manufactured by Amersham Pharmacia Biotech) which had been previously equilibrated with a 10 mM Tris-HCl buffer (pH 7.5) containing 0.1% Triton X-100. Next, the SCDase was eluted with a 10 mM Tris-HCl buffer (pH 7.5) containing 0.1% Triton X-100 and 1M NaCl to collect an active fraction (4). The active fraction (4) collected was used as the purified enzyme preparation.

The purified enzyme preparation obtained showed a single band on SDS-PAGE. The total protein amount was 39.3 mg, and the total activity was 5258 U.

Sequence Free Text

The sequence as shown in SEQ ID NO: 8 shows a sequence of a primer for amplifying the spingolipid ceramide deacylase gene.

The sequence as shown in SEQ ID NO: 9 shows a sequence of a primer for amplifying the spingolipid ceramide deacylase gene.

The sequence as shown in SEQ ID NO: 10 shows a sequence of a primer for amplifying the spingolipid ceramide deacylase gene.

The sequence as shown in SEQ ID NO: 11 shows a sequence of a primer for amplifying the spingolipid ceramide deacylase gene.

The sequence as shown in SEQ ID NO: 12 shows a sequence of a primer for amplifying the spingolipid ceramide deacylase gene.

The sequence as shown in SEQ ID NO: 13 shows a sequence of a primer for amplifying the spingolipid ceramide deacylase gene.

The sequence as shown in SEQ ID NO: 16 shows a sequence of a primer for amplifying the spingolipid ceramide deacylase gene.

The sequence as shown in SEQ ID NO: 17 shows a sequence of a primer for amplifying the spingolipid ceramide deacylase gene.

The sequence as shown in SEQ ID NO: 18 shows a sequence of a primer for amplifying the gene encoding the deletion mutant of spingolipid ceramide deacylase which lacks C-terminal.

The sequence as shown in SEQ ID NO: 19 shows a nucleotide sequence of a primer for amplifying the gene encoding the deletion mutant of spingolipid ceramide deacylase which lacks C-terminal. The above-mentioned sequence corresponds to the sequence of the base numbers: 1 to 2031 in SEQ ID NO: 2.

The sequence as shown in SEQ ID NO: 20 shows an amino acid sequence of a primer for amplifying the gene encoding the deletion mutant of spingolipid ceramide deacylase which lacks C-terminal. The above-mentioned sequence corresponds to the sequence of the amino acid numbers: 1 to 677 in SEQ ID NO: 1.

INDUSTRIAL APPLICABILITY

According to the present invention, the amino acid sequence of the sphingolipid ceramide deacylase and the nucleotide sequence encoding the amino acid sequence are provided for the first time. Accordingly, there are provided a method for producing a polypeptide possessing a sphingolipid ceramide deacylase activity by genetic engineering, using the nucleic acid encoding the polypeptide possessing a sphingolipid ceramide deacylase activity, and a method for detecting the sphingolipid ceramide deacylase. According to the method for producing the sphingolipid ceramide deacylase of the present invention, there are exhibited excellent effects such that the desired sphingolipid ceramide deacylase can easily be purified without the necessity to add a sphingolipid to a medium for inducing expression of the sphingolipid ceramide deacylase, and with no contamination of concurrently induced enzymes such as sphingomyelinase, sphingolipid or a degradation product thereof added to the medium. Also, there are provided a probe and primers, each capable of specifically hybridizing to the nucleic acid encoding the polypeptide of the present invention possessing a sphingolipid ceramide deacylase activity, and an antibody or a fragment thereof, capable of specifically binding to the polypeptide of the present invention possessing a sphingolipid ceramide deacylase activity. The sphingolipid ceramide deacylase can be detected conveniently and highly sensitively using the probe, the primers, and the antibody or a fragment thereof.

The invention claimed is:

1. An isolated polypeptide having the amino acid sequence shown in SEQ ID NO: 20.

2. An isolated nucleic acid selected from the group consisting of the following (A) to (D):
   (A) a nucleic acid encoding a polypeptide having the amino acid sequence shown in SEQ ID NO: 20;
   (B) a nucleic acid having the nucleotide sequence shown in SEQ ID NO: 19;
   (C) a nucleic acid capable of hybridizing under stringent conditions to the nucleic acid of SEQ ID NO:19 or the full complementary strand thereof, wherein stringent conditions comprises incubation at 50° C. for 12 to 20 hours in 6×SSC, 0.5% SDS, 0.1% bovine serum albumin, 0.1% polyvinyl pyrrolidone, 0.1% Ficol 400, and 0.01% salmon sperm DNA and washing at 50° C. in 2×SSC and 0.5% SDS; and
   (D) a nucleic acid having a nucleotide sequence different from the nucleic acid of any one of the above (A) to (C) via degeneracy
   wherein the nucleic acid encodes a polypeptide possessing a sphingolipid ceramide deacylase activity.

3. A recombinant DNA comprising the nucleic acid of claim 2.

4. An isolated cell harboring the nucleic acid of claim 2 or the recombinant DNA of claim 3.

5. A method for producing an isolated polypeptide possessing a sphingolipid ceramide deacylase activity, characterized by culturing the cell of claim 4 under conditions appropriate for expression of the sphingolipid ceramide deacylase, and then collecting the polypeptide possessing a sphingolipid ceramide deacylase activity from the resulting culture.

* * * * *

SEQUENCE LISTING

```
<160> NUMBER OF SEQ ID NOS: 20

<210> SEQ ID NO 1
<211> LENGTH: 954
<212> TYPE: PRT
<213> ORGANISM: Shewanella alga

<400> SEQUENCE: 1

Thr Thr Gln Ala Val Asp Ser Leu Ala Gln Gln Cys Phe Ile Ile Gln
1               5                   10                  15
```

-continued

```
Ser Pro Thr Asn Gly Gln Tyr Leu His Arg Phe His Gln Gly Gly Thr
            20                  25                  30

Val Asp Asp Gly Leu Ser Tyr Arg Phe Asp Asn Ile Ser Gln Ala Glu
            35                  40                  45

Ala Ser Ala Phe Tyr Phe Lys Pro Ser Arg Arg Gly His Phe Met Met
            50                  55                  60

Thr Asp Ala Asp Gly Arg Phe Phe Ala Ser His Leu Pro Ala Glu Val
65                  70                  75                  80

Ser Ala Gly Arg Tyr Pro Gly Glu Phe Ala Glu Trp Arg Val Asp Ala
                85                  90                  95

Glu Thr Ala Pro Ser Gly Glu Phe Ser Tyr Arg Phe His Ala Val Gly
            100                 105                 110

Leu Asn Leu Gly Leu Arg His Asn Tyr Ser Gly Gly Leu Tyr Phe
            115                 120                 125

Phe Asp Leu Leu Asn Pro Gly Asn Asn Thr Ser Glu Ala Ser Phe Lys
130                 135                 140

Leu Val Ala Ser Asp Ala Cys Ser Ala Phe Pro Glu Val Glu Val Asn
145                 150                 155                 160

Ala Ser Gly Asp Phe Ser Ala Leu Lys Gly Asp Ala Ser Leu Pro Val
                165                 170                 175

Arg Gly Leu Val Asp Ala His Thr His Ile Thr Ser Tyr Glu Phe Met
            180                 185                 190

Gly Gly Lys Met Met His Gly Lys Pro Phe His Arg Trp Gly Val Thr
            195                 200                 205

Gln Ala Leu Asn Asp Ser Ala Val Ile His Gly Pro Asn Gly Ser Leu
        210                 215                 220

Asp Leu Ile Gly Asn Leu Tyr Ser Phe Asn Asp Ala Asn Phe Arg Tyr
225                 230                 235                 240

Asp Thr Arg Gly Trp Pro Asp Phe Pro Trp Trp Pro Asn His Glu Gln
                245                 250                 255

Met Thr His Ser Gly Tyr Tyr Tyr Lys Trp Ile Glu Arg Ala Trp Leu
            260                 265                 270

Gly Gly Leu Arg Leu Met Val Thr His Leu Val Glu Asn Glu Val Leu
        275                 280                 285

Cys Asn Ala Gln Lys Thr Ile Asn Pro Ala Ser Trp Val Asn Pro Asn
        290                 295                 300

Asp Cys Asn Thr Met Asn Ser Ile Gln Leu Gln Ile Asn Arg Leu Lys
305                 310                 315                 320

Gln Met Gln Glu Tyr Ile Asp Val Gln Ser Gly Gly Pro Gly Lys Gly
                325                 330                 335

Phe Phe Arg Leu Val Ser Ser Pro Gln Glu Ala Arg Glu Val Ile Ala
            340                 345                 350

Asp Gly Lys Leu Ala Val Leu Met Gly Ile Glu Ala Ser Glu Leu Phe
            355                 360                 365

Asn Cys Gly Ile Lys Asp Asp Cys Asn Arg Arg Gln Ile Glu Glu Gln
        370                 375                 380

Leu Gln Gln Val Tyr Ala Lys Gly Val Arg Ile Leu Phe Pro Thr His
385                 390                 395                 400

Lys Phe Asp Asn Gln Leu Gly Gly Ser Val Val Glu Asp Gly Phe Ile
                405                 410                 415

Asn Ile Gly Glu Val Leu Ala Thr Gly His Phe Phe Glu Thr Gln Ala
            420                 425                 430
```

```
Cys Asp Ala Asp Thr Gln Gly Arg Pro Phe Lys Ser Gly Phe Pro Ile
        435                 440                 445

Leu Gly Glu Ile Pro Val Leu Lys Asp Ile Leu Asn Ala Val Gly Leu
        450                 455                 460

Asn Pro Gln Tyr Asp Glu Asn Met Leu His Cys Asn Lys His Gly Leu
465                 470                 475                 480

Ser Glu Lys Gly Val Tyr Leu Val Asn Arg Met Ile Asp Met Gly Met
                485                 490                 495

Leu Ile Glu Leu Asp His Met Ser Ala Gln Thr Ala Thr Ser Val Met
        500                 505                 510

Asp Ile Val Glu Gln Arg Gln Tyr Gly Gly Val Ile Thr Ser His Ser
        515                 520                 525

Trp Met Thr Asp Gly Thr Gln Gly Arg Leu His Pro Asn Thr Leu Arg
        530                 535                 540

Leu Ala Lys Val Gly Gly Phe Met Ala Pro Tyr Asn Ser Asn Ala Asn
545                 550                 555                 560

His Leu Gly Gly Ser Ile Asp Arg Tyr Leu Gln Leu Ile Ala Asp Thr
                565                 570                 575

Pro Phe Leu Pro Gly Val Gly Leu Gly Thr Asp Met Ser Gly Leu Gly
        580                 585                 590

Ala Gln Ala Gly Pro Arg Asp Asp Ala Ala Thr Asn Pro Leu His Tyr
        595                 600                 605

Pro Phe Val Ser Glu Phe Gly Ile Gln Phe Glu Arg Gln Val Ser Gly
        610                 615                 620

Asn Arg Val Phe Asp Phe Asn Gln Asp Gly Met Ala His Tyr Gly Met
625                 630                 635                 640

Leu Ala Asp His Leu Gln Asp Val Arg Glu Gln Leu Gly Gly Ser Thr
                645                 650                 655

Tyr Glu Ala Leu Met Asn Ser Ala Glu Ala Tyr Leu Gln Met Trp Glu
        660                 665                 670

Arg Ala Glu Ala His Arg Asp Glu Ala Tyr Ile Asn Pro Leu Pro Thr
        675                 680                 685

Tyr Val Arg Ile Val Asn Arg Ala Ser Asp Lys Cys Met Asp Ile Pro
        690                 695                 700

Gly Asn Gly Ser Asp Met Val Asn Gly Thr Asp Val Ile Leu Tyr Asp
705                 710                 715                 720

Cys Glu Arg Asp Ala Trp Asp Gln Arg Trp Ser Phe Asp Ala Asp Lys
                725                 730                 735

Arg Met Phe Ser Asn Lys Ala Asn Pro Ser Leu Cys Leu Asp Asn Arg
        740                 745                 750

Gly Gln Ala Tyr Asn Glu Gly Glu Ile Val Val Trp Glu Cys Val Asp
        755                 760                 765

Ser Asp Asn Leu Arg Trp Asp Tyr Asp Gly Arg Phe Ile Arg Ser Ala
770                 775                 780

His Asp Ala Asn Ile Val Ala Asp Ala Tyr Gly Arg Gly Asn Asp Ala
785                 790                 795                 800

Gln Val Gly Gln Trp Gln Phe His Gly Gly Ala Asn Gln Gln Trp Leu
                805                 810                 815

Leu Arg Pro Glu Met Thr Ile His Arg Trp Val Ser Leu Arg Asp Lys
        820                 825                 830

Arg Ala Gly Leu Cys Ile Ser Ala Pro Glu Gln Ala Gln Ser Gly Ser
        835                 840                 845

Leu Val Asn Leu Asp Asn Cys Ser Asn Arg Gln Gly Gln Lys Trp Tyr
```

```
                850              855            860
Phe Asp Pro Ile Lys Gly Ser Ile Lys Leu Ala Gly Asp Ala Gly Leu
865                      870                875                880

Cys Leu His Ile Pro Gly Gly Asn Thr Gln Asp His Ser Gln Leu Ala
                 885                890                895

Leu Ala Pro Cys Asp Ala Ser Asn Pro Ala Gln Ala Phe Asp Lys Asp
             900                905                910

Gly Ser Val Phe Ser Ser Arg Met Ala Pro Asn Gln Val Leu Asp Ala
         915                920                925

Ser Gly Glu Gln Ala Gly Ala Ala Leu Ile Leu Tyr His His His Gly
    930                935                940

Asp Ser Asn Gln Lys Trp Lys Ser Ser Leu
945                 950
```

<210> SEQ ID NO 2
<211> LENGTH: 2862
<212> TYPE: DNA
<213> ORGANISM: Shewanella alga

<400> SEQUENCE: 2

```
accacccagg cggtcgacag cctggcgcag caatgtttta ttattcaatc gccaaccaat    60
ggccagtatc tgcatcgctt ccatcaggga ggcactgtgg atgatggtct gagttatcgt   120
ttcgataata tcagccaggc cgaggccagt gcgttttact tcaaacccag tcgccgcggt   180
cattttatga tgacagacgc agatggccgc ttctttgcca gccatctgcc ggccgaagtc   240
agcgccggtc gttacccggg ggaatttgcc gagtggcggg ttgacgccga acagcacca   300
tccggtgaat tcagttatcg ctttcacgcc gtgggcctca atctgggact caggcacaac   360
tacagcggcg gaggcttgta tttcttcgat ctgctcaacc ctggaaacaa cacttcagag   420
gcaagcttca agctggttgc cagtgacgcc tgcagcgcgt ttcccgaggt tgaagtcaat   480
gccagtggtg atttctccgc cctgaaaggc gatgcttcac tgccggtgcg gggtctggtc   540
gatgcccaca cccatatcac ctcgtatgag tttatgggcg gcaagatgat gcatggcaag   600
ccgttccacc gctgggggt gacccaggcg ttgaacgaca gtgcggtgat ccatgggccg   660
aatggctcac tggatctcat cggcaatctc tactccttca cgacgccaa cttccgctat   720
gacacccgag gctggccgga cttcccctgg tgcccaatc gagcagat gacccactca   780
ggttactact acaagtggat tgagcgcgcc tggctaggcg gtttgcgcct gatggtcacc   840
catctggtgg aaaacgaggt gttgtgcaac gcccagaaaa ccatcaatcc cgccagttgg   900
gtcaaccccca cgactgtaa caccatgaac agcattcagt tgcagattaa ccgtctcaag   960
caaatgcagg agtatattga tgtgcagtcc ggcggccccg gcaaaggctt cttccgcctg  1020
gtgtcctcgc ctcaagaggc tcgcgaggtc attgccgacg gcaagctggc ggtgctgatg  1080
ggcatagagg cctcagagct gttcaactgc ggtatcaagg atgattgcaa ccgccgccag  1140
attgaagagc aactgcagca agtttatgcc aaggggtga gaatcctgtt cccgacccac  1200
aagttcgata ccaactggg cggctcagtg gtggaagacg gctttatcaa tatcggtgaa  1260
gtcttggcga cgggccattt ctttgaaacc caggcctgcg acgccgacac ccagggcaga  1320
ccattcaagt ccggtttccc catttggggc gaaatcccag tgctcaagga tattctcaat  1380
gccgtgggtc tcaatcccca gtacgacgag aacatgctgc actgcaacaa gcatggcttg  1440
tccgaaaaag cgtctacct ggttaaccgc atgatagata tggaatgtt gatagaattg  1500
gatcatatgt cggcacaaac cgccaccagt gtgatggata ttgtcgagca gcgccaatat  1560
```

-continued

```
ggcggggtga tcaccagcca cagctggatg actgatggca cccaaggcag actgcacccc      1620
aacaccctgc gcctggccaa ggtcggcggt tttatggcgc cctacaacag taacgccaac      1680
catcttggag gcagtattga tagatacctg cagttgatag ccgatactcc ttttctgccg      1740
ggtgtcggcc tgggaaccga tatgagtggc ctcggcgctc aggccggtcc cagagacgat      1800
gcggccacta tccactgca ctacccttc gtcagtgagt tcggtatcca gtttgagcgt       1860
caggtatcgg ggaatcgtgt atttgacttc aatcaggatg gcatggccca ttacggtatg      1920
ctggctgatc atctgcagga tgtgcgcgag cagcttggcg gcagtaccta tgaagccttg      1980
atgaactcgg ccgaagccta tctgcagatg tgggagcgcg cagaagccca cagggatgaa      2040
gcctatatca atccactgcc gacctatgtg cggatagtca accgcgcctc ggacaagtgt      2100
atggatattc cgggtaatgg cagcgatatg gtcaatggca cagatgtgat cctctatgat      2160
tgtgaacgcg acgcctggga tcaacgctgg agctttgatg ccgacaaacg catgttcagc      2220
aacaaagcca atccatcctt gtgtttggac aatcgcggtc aggcctacaa tgaaggcgaa      2280
atcgtggtat gggagtgtgt cgacagcgac aatctgcgtt gggattatga cggccgcttt      2340
attcgcagtg cccatgacgc caatatagtg gccgacgcct atggccgtgg caacgatgcc      2400
caagtgggtc aatggcaatt tcatggcggc gccaaccagc aatggttgct caggcctgag      2460
atgactattc accgctgggt cagtttgcgg gataaacgtg ccgggctatg tatcagcgct      2520
cccgaacagg cccaaagcgg cagcctggtg aacctggaca actgcagcaa ccgtcagggg      2580
caaaaatggt acttcgatcc gataaaaggc agtatcaaac tggctggtga cgcgggactg      2640
tgcctgcaca ttccgggtgg caatacccag gatcatagcc agttggcact ggcgccctgc      2700
gatgcttcca atccggctca ggcattcgat aaagacggca gcgtgttctc aagccgaatg      2760
gcacccaatc aggtgcttga tgcctcggga gaacaagccg gcgcggctct gatcctctac      2820
caccaccatg gcgacagtaa tcagaagtgg aagtccagcc tc                         2862
```

<210> SEQ ID NO 3
<211> LENGTH: 16
<212> TYPE: PRT
<213> ORGANISM: Shewanella alga

<400> SEQUENCE: 3

Gln Met Gln Glu Tyr Ile Asp Val Gln Ser Gly Gly Pro Gly Lys Gly
1               5                   10                  15

<210> SEQ ID NO 4
<211> LENGTH: 12
<212> TYPE: PRT
<213> ORGANISM: Shewanella alga

<400> SEQUENCE: 4

Arg Leu Met Val Thr His Leu Val Glu Asn Glu Val
1               5                   10

<210> SEQ ID NO 5
<211> LENGTH: 7
<212> TYPE: PRT
<213> ORGANISM: Shewanella alga

<400> SEQUENCE: 5

Gln Leu Gln Gln Val Tyr Ala
1               5

```
<210> SEQ ID NO 6
<211> LENGTH: 7
<212> TYPE: PRT
<213> ORGANISM: Shewanella alga

<400> SEQUENCE: 6

Gly Val Arg Ile Leu Phe Pro
1               5

<210> SEQ ID NO 7
<211> LENGTH: 18
<212> TYPE: PRT
<213> ORGANISM: Shewanella alga

<400> SEQUENCE: 7

Thr Thr Gln Ala Val Asp Ser Leu Ala Gln Gln Cys Phe Ile Ile Gln
1               5                   10                  15

Ser Pro

<210> SEQ ID NO 8
<211> LENGTH: 20
<212> TYPE: DNA
<213> ORGANISM: Artificial Sequence
<220> FEATURE:
<223> OTHER INFORMATION: Primer for amplifying SCDase gene.

<400> SEQUENCE: 8
carcartgyt tyathathca                                           20

<210> SEQ ID NO 9
<211> LENGTH: 17
<212> TYPE: DNA
<213> ORGANISM: Artificial Sequence
<220> FEATURE:
<223> OTHER INFORMATION: Primer for amplifying SCDase gene.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 9
ttngcncarc artgytt                                              17

<210> SEQ ID NO 10
<211> LENGTH: 17
<212> TYPE: DNA
<213> ORGANISM: Artificial Sequence
<220> FEATURE:
<223> OTHER INFORMATION: Primer for amplifying SCDase gene.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 10
ctngcncarc artgytt                                              17

<210> SEQ ID NO 11
<211> LENGTH: 17
<212> TYPE: DNA
```

```
<213> ORGANISM: Artificial Sequence
<220> FEATURE:
<223> OTHER INFORMATION: Primer for amplifying SCDase gene.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 11
ccnstytgna crtcdat                                                 17

<210> SEQ ID NO 12
<211> LENGTH: 17
<212> TYPE: DNA
<213> ORGANISM: Artificial Sequence
<220> FEATURE:
<223> OTHER INFORMATION: Primer for amplifying SCDase gene.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 12
ccnsaytgna crtcdat                                                 17

<210> SEQ ID NO 13
<211> LENGTH: 20
<212> TYPE: DNA
<213> ORGANISM: Artificial Sequence
<220> FEATURE:
<223> OTHER INFORMATION: Primer for amplifying SCDase gene.

<400> SEQUENCE: 13
acrtcdatrt aytcytgcat                                              20

<210> SEQ ID NO 14
<211> LENGTH: 992
<212> TYPE: PRT
<213> ORGANISM: Shewanella alga

<400> SEQUENCE: 14

Met Lys Lys Leu Ile Gly His Gly Asp Trp Pro Ser Ala Lys Ser Leu
1               5                   10                  15

Phe Ser Ala Leu Ile Pro Gly Leu Phe Thr Leu Gly Thr Leu Pro Leu
            20                  25                  30

Ala Ala Ala Glu Thr Gln Thr Thr Gln Ala Val Asp Ser Leu Ala Gln
        35                  40                  45

Gln Cys Phe Ile Ile Gln Ser Pro Thr Asn Gly Gln Tyr Leu His Arg
    50                  55                  60

Phe His Gln Gly Gly Thr Val Asp Asp Gly Leu Ser Tyr Arg Phe Asp
65                  70                  75                  80

Asn Ile Ser Gln Ala Glu Ala Ser Ala Phe Tyr Phe Lys Pro Ser Arg
                85                  90                  95

Arg Gly His Phe Met Met Thr Asp Ala Asp Gly Arg Phe Phe Ala Ser
            100                 105                 110

His Leu Pro Ala Glu Val Ser Ala Gly Arg Tyr Pro Gly Glu Phe Ala
        115                 120                 125
```

-continued

Glu Trp Arg Val Asp Ala Glu Thr Ala Pro Ser Gly Glu Phe Ser Tyr
130                 135                 140

Arg Phe His Ala Val Gly Leu Asn Leu Gly Leu Arg His Asn Tyr Ser
145                 150                 155                 160

Gly Gly Gly Leu Tyr Phe Phe Asp Leu Leu Asn Pro Gly Asn Asn Thr
                165                 170                 175

Ser Glu Ala Ser Phe Lys Leu Val Ala Ser Asp Ala Cys Ser Ala Phe
            180                 185                 190

Pro Glu Val Glu Val Asn Ala Ser Gly Asp Phe Ser Ala Leu Lys Gly
        195                 200                 205

Asp Ala Ser Leu Pro Val Arg Gly Leu Val Asp Ala His Thr His Ile
210                 215                 220

Thr Ser Tyr Glu Phe Met Gly Gly Lys Met Met His Gly Lys Pro Phe
225                 230                 235                 240

His Arg Trp Gly Val Thr Gln Ala Leu Asn Asp Ser Ala Val Ile His
                245                 250                 255

Gly Pro Asn Gly Ser Leu Asp Leu Ile Gly Asn Leu Tyr Ser Phe Asn
            260                 265                 270

Asp Ala Asn Phe Arg Tyr Asp Thr Arg Gly Trp Pro Asp Phe Pro Trp
        275                 280                 285

Trp Pro Asn His Glu Gln Met Thr His Ser Gly Tyr Tyr Tyr Lys Trp
290                 295                 300

Ile Glu Arg Ala Trp Leu Gly Gly Leu Arg Leu Met Val Thr His Leu
305                 310                 315                 320

Val Glu Asn Glu Val Leu Cys Asn Ala Gln Lys Thr Ile Asn Pro Ala
                325                 330                 335

Ser Trp Val Asn Pro Asn Asp Cys Asn Thr Met Asn Ser Ile Gln Leu
            340                 345                 350

Gln Ile Asn Arg Leu Lys Gln Met Gln Glu Tyr Ile Asp Val Gln Ser
        355                 360                 365

Gly Gly Pro Gly Lys Gly Phe Phe Arg Leu Val Ser Ser Pro Gln Glu
370                 375                 380

Ala Arg Glu Val Ile Ala Asp Gly Lys Leu Ala Val Leu Met Gly Ile
385                 390                 395                 400

Glu Ala Ser Glu Leu Phe Asn Cys Gly Ile Lys Asp Asp Cys Asn Arg
                405                 410                 415

Arg Gln Ile Glu Glu Gln Leu Gln Gln Val Tyr Ala Lys Gly Val Arg
            420                 425                 430

Ile Leu Phe Pro Thr His Lys Phe Asp Asn Gln Leu Gly Gly Ser Val
        435                 440                 445

Val Glu Asp Gly Phe Ile Asn Ile Gly Glu Val Leu Ala Thr Gly His
450                 455                 460

Phe Phe Glu Thr Gln Ala Cys Asp Ala Asp Thr Gln Gly Arg Pro Phe
465                 470                 475                 480

Lys Ser Gly Phe Pro Ile Leu Gly Glu Ile Pro Val Leu Lys Asp Ile
                485                 490                 495

Leu Asn Ala Val Gly Leu Asn Pro Gln Tyr Asp Glu Asn Met Leu His
            500                 505                 510

Cys Asn Lys His Gly Leu Ser Glu Lys Gly Val Tyr Leu Val Asn Arg
        515                 520                 525

Met Ile Asp Met Gly Met Leu Ile Glu Leu Asp His Met Ser Ala Gln
530                 535                 540

-continued

```
Thr Ala Thr Ser Val Met Asp Ile Val Glu Gln Arg Gln Tyr Gly Gly
545                 550                 555                 560

Val Ile Thr Ser His Ser Trp Met Thr Asp Thr Gln Gly Arg Leu
                565                 570                 575

His Pro Asn Thr Leu Arg Leu Ala Lys Val Gly Gly Phe Met Ala Pro
            580                 585                 590

Tyr Asn Ser Asn Ala Asn His Leu Gly Gly Ser Ile Asp Arg Tyr Leu
        595                 600                 605

Gln Leu Ile Ala Asp Thr Pro Phe Leu Pro Gly Val Gly Leu Gly Thr
    610                 615                 620

Asp Met Ser Gly Leu Gly Ala Gln Ala Gly Pro Arg Asp Asp Ala Ala
625                 630                 635                 640

Thr Asn Pro Leu His Tyr Pro Phe Val Ser Glu Phe Gly Ile Gln Phe
                645                 650                 655

Glu Arg Gln Val Ser Gly Asn Arg Val Phe Asp Phe Asn Gln Asp Gly
            660                 665                 670

Met Ala His Tyr Gly Met Leu Ala Asp His Leu Gln Asp Val Arg Glu
        675                 680                 685

Gln Leu Gly Gly Ser Thr Tyr Glu Ala Leu Met Asn Ser Ala Glu Ala
    690                 695                 700

Tyr Leu Gln Met Trp Glu Arg Ala Glu Ala His Arg Asp Glu Ala Tyr
705                 710                 715                 720

Ile Asn Pro Leu Pro Thr Tyr Val Arg Ile Val Asn Arg Ala Ser Asp
                725                 730                 735

Lys Cys Met Asp Ile Pro Gly Asn Gly Ser Asp Met Val Asn Gly Thr
            740                 745                 750

Asp Val Ile Leu Tyr Asp Cys Glu Arg Asp Ala Trp Asp Gln Arg Trp
        755                 760                 765

Ser Phe Asp Ala Asp Lys Arg Met Phe Ser Asn Lys Ala Asn Pro Ser
    770                 775                 780

Leu Cys Leu Asp Asn Arg Gly Gln Ala Tyr Asn Glu Gly Glu Ile Val
785                 790                 795                 800

Val Trp Glu Cys Val Asp Ser Asp Asn Leu Arg Trp Asp Tyr Asp Gly
                805                 810                 815

Arg Phe Ile Arg Ser Ala His Asp Ala Asn Ile Val Ala Asp Ala Tyr
            820                 825                 830

Gly Arg Gly Asn Asp Ala Gln Val Gly Gln Trp Gln Phe His Gly Gly
        835                 840                 845

Ala Asn Gln Gln Trp Leu Leu Arg Pro Glu Met Thr Ile His Arg Trp
850                 855                 860

Val Ser Leu Arg Asp Lys Arg Ala Gly Leu Cys Ile Ser Ala Pro Glu
865                 870                 875                 880

Gln Ala Gln Ser Gly Ser Leu Val Asn Leu Asp Asn Cys Ser Asn Arg
            885                 890                 895

Gln Gly Gln Lys Trp Tyr Phe Asp Pro Ile Lys Gly Ser Ile Lys Leu
        900                 905                 910

Ala Gly Asp Ala Gly Leu Cys Leu His Ile Pro Gly Gly Asn Thr Gln
    915                 920                 925

Asp His Ser Gln Leu Ala Leu Ala Pro Cys Asp Ala Ser Asn Pro Ala
930                 935                 940

Gln Ala Phe Asp Lys Asp Gly Ser Val Phe Ser Ser Arg Met Ala Pro
945                 950                 955                 960

Asn Gln Val Leu Asp Ala Ser Gly Glu Gln Ala Gly Ala Ala Leu Ile
```

```
                965               970              975
Leu Tyr His His His Gly Asp Ser Asn Gln Lys Trp Lys Ser Ser Leu
        980                 985                 990

<210> SEQ ID NO 15
<211> LENGTH: 2976
<212> TYPE: DNA
<213> ORGANISM: Shewanella alga

<400> SEQUENCE: 15
atgaaaaagc taatcggaca tggagattgg cccagtgcca aaagtctgtt ctctgccctg      60
atccccggcc tgtttacgct gggaacccta ccctagctg cagctgaaac gcaaaccacc     120
caggcggtcg acagcctggc gcagcaatgt tttattattc aatcgccaac caatggccag    180
tatctgcatc gcttccatca gggaggcact gtggatgatg gtctgagtta tcgtttcgat    240
aatatcagcc aggccgaggc cagtgcgttt acttcaaac ccagtcgccg cggtcatttt     300
atgatgacag acgcagatgg ccgcttcttt gccagccatc tgccggccga agtcagcgcc    360
ggtcgttacc cggggggaatt tgccgagtgg cgggttgacg ccgaaacagc accatccggt   420
gaattcagtt atcgctttca cgccgtgggc ctcaatctgg gactcaggca aactacagc     480
ggcggaggct tgtatttctt cgatctgctc aaccctggaa caacacttc agaggcaagc    540
ttcaagctgg ttgccagtga cgcctgcagc gcgtttcccg aggttgaagt caatgccagt   600
ggtgatttct ccgccctgaa aggcgatgct tcactgccgg tgcggggtct ggtcgatgcc   660
cacacccata tcacctcgta tgagtttatg gcggcaaga tgatgcatgg caagccgttc    720
caccgctggg gggtgaccca ggcgttgaac gacagtgcgg tgatccatgg gccgaatggc   780
tcactggatc tcatcggcaa tctctactcc ttcaacgacg ccaacttccg ctatgacacc   840
cgaggctggc cggacttccc ctggtggccc aatcacgagc agatgaccca ctcaggttac   900
tactacaagt ggattgagcg cgcctggcta ggcggttttgc gcctgatggt cacccatctg   960
gtggaaaacg aggtgttgtg caacgcccag aaaaccatca atcccgccag ttgggtcaac   1020
cccaacgact gtaacaccat gaacagcatt cagttgcaga ttaaccgtct caagcaaatg   1080
caggagtata ttgatgtgca gtccggcggc cccggcaaag gcttcttccg cctggtgtcc   1140
tcgcctcaag aggctcgcga ggtcattgcc gacggcaagc tggcggtgct gatgggcata   1200
gaggcctcag agctgttcaa ctgcggtatc aaggatgatt gcaaccgccg ccagattgaa   1260
gagcaactgc agcaagttta tgccaagggg gtgagaatcc tgttcccgac ccacaagttc   1320
gataaccaac tgggcggctc agtggtggaa gacggcttta tcaatatcgg tgaagtcttg   1380
gcgacgggcc atttcttga aacccaggcc tgcgacgccg acacccaggg cagaccattc    1440
aagtccggtt tccccatttt gggcgaaatc ccagtgctca aggatattct caatgccgtg   1500
ggtctcaatc cccagtacga cgagaacatg ctgcactgca caagcatgg cttgtccgaa    1560
aaaggcgtct acctggttaa ccgcatgata gatatgggaa tgttgataga attggatcat   1620
atgtcggcac aaaccgccac cagtgtgatg gatattgtcg agcagcgcca atatggcggg   1680
gtgatcacca gccacagctg gatgactgat ggcacccaag gcagactgca ccccaacacc   1740
ctgcgcctgg ccaaggtcgg cggttttat gcgcccctaca acgtaacgc caaccatctt    1800
ggaggcagta ttgatagata cctgcagttg atagccgata ctccttttct gccgggtgtc   1860
ggcctgggaa ccgatatgag tggcctcggc gctcaggccg gtcccagaga cgatgcggcc   1920
actaatccac tgcactaccc cttcgtcagt gagttcggta tccagtttga gcgtcaggta   1980
```

```
tcggggaatc gtgtatttga cttcaatcag gatggcatgg cccattacgg tatgctggct      2040
gatcatctgc aggatgtgcg cgagcagctt ggcggcagta cctatgaagc cttgatgaac      2100
tcggccgaag cctatctgca gatgtgggag cgcgcagaag cccacaggga tgaagcctat      2160
atcaatccac tgccgaccta tgtgcggata gtcaaccgcg cctcggacaa gtgtatggat      2220
attccgggta atggcagcga tatggtcaat ggcacagatg tgatcctcta tgattgtgaa      2280
cgcgacgcct gggatcaacg ctggagcttt gatgccgaca aacgcatgtt cagcaacaaa      2340
gccaatccat ccttgtgttt ggacaatcgc ggtcaggcct acaatgaagg cgaaatcgtg      2400
gtatgggagt gtgtcgacag cgacaatctg cgttgggatt atgacggccg ctttattcgc      2460
agtgcccatg acgccaatat agtggccgac gcctatggcc gtggcaacga tgcccaagtg      2520
ggtcaatggc aatttcatgg cggcgccaac cagcaatggt tgctcaggcc tgagatgact      2580
attcaccgct gggtcagttt gcgggataaa cgtgccgggc tatgtatcag cgctcccgaa      2640
caggcccaaa gcggcagcct ggtgaacctg acaactgca gcaaccgtca ggggcaaaaa      2700
tggtacttcg atccgataaa aggcagtatc aaactggctg gtgacgcggg actgtgcctg      2760
cacattccgg gtggcaatac ccaggatcat agccagttgg cactggcgcc ctgcgatgct      2820
tccaatccgg ctcaggcatt cgataaagac ggcagcgtgt tctcaagccg aatggcaccc      2880
aatcaggtgc ttgatgcctc gggagaacaa gccggcgcgg ctctgatcct ctaccaccac      2940
catggcgaca gtaatcagaa gtggaagtcc agcctc                                2976

<210> SEQ ID NO 16
<211> LENGTH: 30
<212> TYPE: DNA
<213> ORGANISM: Artificial Sequence
<220> FEATURE:
<223> OTHER INFORMATION: Primer for amplifying SCDase gene.

<400> SEQUENCE: 16
gacgctagca tgaaaaagct aatcggacat                                            30

<210> SEQ ID NO 17
<211> LENGTH: 32
<212> TYPE: DNA
<213> ORGANISM: Artificial Sequence
<220> FEATURE:
<223> OTHER INFORMATION: Primer for amplifying SCDase gene.

<400> SEQUENCE: 17
cttctcgaga ggaggctgga cttccacttc tg                                         32

<210> SEQ ID NO 18
<211> LENGTH: 30
<212> TYPE: DNA
<213> ORGANISM: Artificial Sequence
<220> FEATURE:
<223> OTHER INFORMATION: Primer for amplifying SCDase gene.

<400> SEQUENCE: 18
gtgctcgagg tgggcttctg cgcgctccca                                            30

<210> SEQ ID NO 19
<211> LENGTH: 2031
<212> TYPE: DNA
<213> ORGANISM: Artificial Sequence
<220> FEATURE:
<223> OTHER INFORMATION: Primer for amplifying SCDase gene. 3'-terminus
      truncated SCDase gene. The sequence corresponding to a sequence
      of base numbers 1 to 2031 in SEQ ID NO:2.
```

-continued

<400> SEQUENCE: 19

```
accacccagg cggtcgacag cctggcgcag caatgtttta ttattcaatc gccaaccaat      60
ggccagtatc tgcatcgctt ccatcaggga ggcactgtgg atgatggtct gagttatcgt     120
ttcgataata tcagccaggc cgaggccagt gcgttttact tcaaacccag tcgccgcggt     180
cattttatga tgacagacgc agatggccgc ttctttgcca gccatctgcc ggccgaagtc     240
agcgccggtc gttacccggg ggaatttgcc gagtggcggg ttgacgccga acagcacca     300
tccggtgaat tcagttatcg ctttcacgcc gtgggcctca atctgggact caggcacaac     360
tacagcggcg gaggcttgta tttcttcgat ctgctcaacc ctggaaacaa cacttcagag     420
gcaagcttca agctggttgc cagtgacgcc tgcagcgcgt ttcccgaggt tgaagtcaat     480
gccagtggtg atttctccgc cctgaaaggc gatgcttcac tgccggtgcg gggtctggtc     540
gatgcccaca cccatatcac ctcgtatgag tttatgggcg gcaagatgat gcatggcaag     600
ccgttccacc gctgggggt gacccaggcg ttgaacgaca gtgcggtgat ccatgggccg     660
aatggctcac tggatctcat cggcaatctc tactccttca cgacgccaa cttccgctat     720
gacacccgag gctggccgga cttcccctgg tgcccaatc acgagcagat gacccactca     780
ggttactact acaagtggat tgagcgcgcc tggctaggcg gtttgcgcct gatggtcacc     840
catctggtgg aaaacgaggt gttgtgcaac gcccagaaaa ccatcaatcc cgccagttgg     900
gtcaaccca cgactgtaa caccatgaac agcattcagt tgcagattaa ccgtctcaag     960
caaatgcagg agtatattga tgtgcagtcc ggcggcccg gcaaaggctt cttccgcctg    1020
gtgtcctcgc ctcaagaggc tcgcgaggtc attgccgacg gcaagctggc ggtgctgatg    1080
ggcatagagg ccctcagagct gttcaactgc ggtatcaagg atgattgcaa ccgccgccag    1140
attgaagagc aactgcagca agtttatgcc aaggggtga aatcctgtt cccgacccac    1200
aagttcgata ccaactggg cggctcagtg gtggaagacg gctttatcaa tatcggtgaa    1260
gtcttggcga cgggccattt ctttgaaacc caggcctgcg acgccgacac ccaggcagaa    1320
ccattcaagt ccggtttccc cattttgggc gaaatcccag tgctcaagga tattctcaat    1380
gccgtgggtc tcaatcccca gtacgacgag aacatgctgc actgcaacaa gcatggcttg    1440
tccgaaaaag cgtctacct ggttaaccgc atgatagata tgggaatgtt gatagaattg    1500
gatcatatgt cggcacaaac cgccaccagt gtgatggata ttgtcgagca gcgccaatat    1560
ggcggggtga tcaccagcca cagctggatg actgatggca cccaaggcag actgcaccc    1620
aacaccctgc gcctggccaa ggtcggcggt tttatggcgc cctacaacag taacgccaac    1680
catcttggag gcagtattga tagatacctg cagttgatag ccgatactcc ttttctgccg    1740
ggtgtcggcc tgggaaccga tatgagtggc ctcggcgctc aggccggtcc cagagacgat    1800
gcggccacta atccactgca ctaccccttc gtcagtgagt tcggtatcca gtttgagcgt    1860
caggtatcgg ggaatcgtgt atttgacttc aatcaggatg gcatggccca ttacggtatg    1920
ctggctgatc atctgcagga tgtgcgcgag cagcttggcg gcagtaccta tgaagccttg    1980
atgaactcgg ccgaagccta tctgcagatg tgggagcgcg cagaagccca c             2031
```

<210> SEQ ID NO 20
<211> LENGTH: 677
<212> TYPE: PRT
<213> ORGANISM: Artificial Sequence
<220> FEATURE:
<223> OTHER INFORMATION: C-terminus truncated SCdase gene. The sequence
      corresponds to a sequence of amino acid numbers 1to 677 in SEQ ID

NO:1.

<400> SEQUENCE: 20

```
Thr Thr Gln Ala Val Asp Ser Leu Ala Gln Gln Cys Phe Ile Ile Gln
  1               5                  10                  15

Ser Pro Thr Asn Gly Gln Tyr Leu His Arg Phe His Gln Gly Gly Thr
             20                  25                  30

Val Asp Asp Gly Leu Ser Tyr Arg Phe Asp Asn Ile Ser Gln Ala Glu
         35                  40                  45

Ala Ser Ala Phe Tyr Phe Lys Pro Ser Arg Arg Gly His Phe Met Met
 50                  55                  60

Thr Asp Ala Asp Gly Arg Phe Phe Ala Ser His Leu Pro Ala Glu Val
 65                  70                  75                  80

Ser Ala Gly Arg Tyr Pro Gly Glu Phe Ala Glu Trp Arg Val Asp Ala
                 85                  90                  95

Glu Thr Ala Pro Ser Gly Glu Phe Ser Tyr Arg Phe His Ala Val Gly
                100                 105                 110

Leu Asn Leu Gly Leu Arg His Asn Tyr Ser Gly Gly Gly Leu Tyr Phe
            115                 120                 125

Phe Asp Leu Leu Asn Pro Gly Asn Asn Thr Ser Glu Ala Ser Phe Lys
130                 135                 140

Leu Val Ala Ser Asp Ala Cys Ser Ala Phe Pro Glu Val Glu Val Asn
145                 150                 155                 160

Ala Ser Gly Asp Phe Ser Ala Leu Lys Gly Asp Ala Ser Leu Pro Val
                165                 170                 175

Arg Gly Leu Val Asp Ala His Thr His Ile Thr Ser Tyr Glu Phe Met
                180                 185                 190

Gly Gly Lys Met Met His Gly Lys Pro Phe His Arg Trp Gly Val Thr
            195                 200                 205

Gln Ala Leu Asn Asp Ser Ala Val Ile His Gly Pro Asn Gly Ser Leu
210                 215                 220

Asp Leu Ile Gly Asn Leu Tyr Ser Phe Asn Asp Ala Asn Phe Arg Tyr
225                 230                 235                 240

Asp Thr Arg Gly Trp Pro Asp Phe Pro Trp Trp Pro Asn His Glu Gln
                245                 250                 255

Met Thr His Ser Gly Tyr Tyr Lys Trp Ile Glu Arg Ala Trp Leu
            260                 265                 270

Gly Gly Leu Arg Leu Met Val Thr His Leu Val Glu Asn Glu Val Leu
            275                 280                 285

Cys Asn Ala Gln Lys Thr Ile Asn Pro Ala Ser Trp Val Asn Pro Asn
290                 295                 300

Asp Cys Asn Thr Met Asn Ser Ile Gln Leu Gln Ile Asn Arg Leu Lys
305                 310                 315                 320

Gln Met Gln Glu Tyr Ile Asp Val Gln Ser Gly Gly Pro Gly Lys Gly
                325                 330                 335

Phe Phe Arg Leu Val Ser Ser Pro Gln Glu Ala Arg Glu Val Ile Ala
            340                 345                 350

Asp Gly Lys Leu Ala Val Leu Met Gly Ile Glu Ala Ser Glu Leu Phe
            355                 360                 365

Asn Cys Gly Ile Lys Asp Asp Cys Asn Arg Arg Gln Ile Glu Glu Gln
370                 375                 380

Leu Gln Gln Val Tyr Ala Lys Gly Val Arg Ile Leu Phe Pro Thr His
385                 390                 395                 400
```

-continued

```
Lys Phe Asp Asn Gln Leu Gly Gly Ser Val Val Glu Asp Gly Phe Ile
            405                 410                 415
Asn Ile Gly Glu Val Leu Ala Thr Gly His Phe Phe Glu Thr Gln Ala
            420                 425                 430
Cys Asp Ala Asp Thr Gln Gly Arg Pro Phe Lys Ser Gly Phe Pro Ile
            435                 440                 445
Leu Gly Glu Ile Pro Val Leu Lys Asp Ile Leu Asn Ala Val Gly Leu
    450                 455                 460
Asn Pro Gln Tyr Asp Glu Asn Met Leu His Cys Asn Lys His Gly Leu
465                 470                 475                 480
Ser Glu Lys Gly Val Tyr Leu Val Asn Arg Met Ile Asp Met Gly Met
            485                 490                 495
Leu Ile Glu Leu Asp His Met Ser Ala Gln Thr Ala Thr Ser Val Met
            500                 505                 510
Asp Ile Val Glu Gln Arg Gln Tyr Gly Gly Val Ile Thr Ser His Ser
            515                 520                 525
Trp Met Thr Asp Gly Thr Gln Gly Arg Leu His Pro Asn Thr Leu Arg
    530                 535                 540
Leu Ala Lys Val Gly Gly Phe Met Ala Pro Tyr Asn Ser Asn Ala Asn
545                 550                 555                 560
His Leu Gly Gly Ser Ile Asp Arg Tyr Leu Gln Leu Ile Ala Asp Thr
            565                 570                 575
Pro Phe Leu Pro Gly Val Gly Leu Gly Thr Asp Met Ser Gly Leu Gly
            580                 585                 590
Ala Gln Ala Gly Pro Arg Asp Asp Ala Ala Thr Asn Pro Leu His Tyr
    595                 600                 605
Pro Phe Val Ser Glu Phe Gly Ile Gln Phe Glu Arg Gln Val Ser Gly
            610                 615                 620
Asn Arg Val Phe Asp Phe Asn Gln Asp Gly Met Ala His Tyr Gly Met
625                 630                 635                 640
Leu Ala Asp His Leu Gln Asp Val Arg Glu Gln Leu Gly Gly Ser Thr
            645                 650                 655
Tyr Glu Ala Leu Met Asn Ser Ala Glu Ala Tyr Leu Gln Met Trp Glu
            660                 665                 670
Arg Ala Glu Ala His
            675
```